United States Patent
King et al.

(10) Patent No.: US 9,921,221 B2
(45) Date of Patent: Mar. 20, 2018

(54) PREDICTING AND TREATING DIABETIC COMPLICATIONS

(71) Applicant: Joslin Diabetes Center, Inc., Boston, MA (US)

(72) Inventors: George L. King, Dover, MA (US); Hillary A. Keenan, Watertown, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 147 days.

(21) Appl. No.: 14/417,023

(22) PCT Filed: Jul. 26, 2013

(86) PCT No.: PCT/US2013/052249
§ 371 (c)(1),
(2) Date: Jan. 23, 2015

(87) PCT Pub. No.: WO2014/018851
PCT Pub. Date: Jan. 30, 2014

(65) Prior Publication Data
US 2015/0204874 A1    Jul. 23, 2015

Related U.S. Application Data

(60) Provisional application No. 61/676,057, filed on Jul. 26, 2012.

(51) Int. Cl.
| | |
|---|---|
| *A61K 48/00* | (2006.01) |
| *C12Q 1/68* | (2006.01) |
| *G01N 33/00* | (2006.01) |
| *G01N 33/53* | (2006.01) |
| *G01N 33/573* | (2006.01) |
| *A61K 38/45* | (2006.01) |
| *A61K 45/06* | (2006.01) |
| *C12N 15/113* | (2010.01) |

(52) U.S. Cl.
CPC .......... *G01N 33/573* (2013.01); *A61K 38/45* (2013.01); *A61K 45/06* (2013.01); *C12N 15/1137* (2013.01); *C12Q 1/6883* (2013.01); *C12N 2310/122* (2013.01); *C12N 2310/14* (2013.01); *C12Q 2600/158* (2013.01); *C12Y 207/0104* (2013.01); *G01N 2333/91215* (2013.01); *G01N 2800/042* (2013.01); *G01N 2800/347* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 4,868,116 A | 9/1989 | Morgan et al. | |
| 4,980,286 A | 12/1990 | Morgan et al. | |
| 5,328,470 A | 7/1994 | Mabel et al. | |
| 2004/0115631 A1* | 6/2004 | Rapp ................ | C12Y 207/0104 435/6.11 |
| 2011/0236913 A1 | 9/2011 | Baek et al. | |
| 2012/0108631 A1 | 5/2012 | Becker et al. | |

FOREIGN PATENT DOCUMENTS

| | | |
|---|---|---|
| WO | 9106309 | 5/1991 |
| WO | 2010040571 A2 | 4/2010 |
| WO | 2012056319 A1 | 5/2012 |
| WO | 2012078618 A2 | 6/2012 |
| WO | 2012092442 A1 | 7/2012 |
| WO | 2012151451 A1 | 11/2012 |

OTHER PUBLICATIONS

Diabetic Nephropathy, Merck Manual, pp. 1-7, accessed Dec. 13, 2016 at URL merckmanuals.com/professional/genitourinary-disorders/glomerular-disorders/diabetic-nephropathy.*
Iori, et al. "Glycolytic enzyme expression and pyruvate kinase activity in cultured fibroblasts from type 1 diabetic patients with and without nephropathy" Biochimica et Biophysica Acta; 2008; vol. 1782; pp. 627-633.
Danos, et al. "Safe and efficient generation of recombinant retroviruses with amphotropic and ecotropic host ranges" Proc. Natl. Academy Science; Sep. 1988; vol. 85; pp. 6460-6464.
Wilson, et al. "Retrovirus-mediated transduction of adult hepatocytes" Proc. Natl. Academy Science; May 1988; vol. 85; pp. 3014-3018.
Chen, et al. "Gene therapy for brain tumors: Regression of experimental gliomas by adenovirus-mediated gene transfer in vivo" Proc. Natl. Academy Science; Apr. 1994; vol. 91; pp. 3054-3057.
Tam, et al. "Stabilized plasmid-lipid particles for systemic gene therapy" Gene Therapy; Jan. 31, 2000; vol. 7; pp. 1867-1874.
Tervaert, et al. "Pathologic Classification of Diabetic Nephropathy" Journal American Soc. Nephrol; 2010; vol. 21; pp. 556-563.
Gao, et al. "Label-free Quantitative Analysis of One-dimensional PAGE LC/MS/MS Proteome" Molecular Cell Proteomics; Dec. 2008; vol. 7; No. 12; pp. 2399-2409.
Gao, et al. Characterization of the Vitreous Proteome in Diabetes without Diabetic Retinopathy and Diabetes with Proliferative Diabetic Retinopathy: Journal of proteome research; Feb. 12, 2008; vol. 7; pp. 2516-2525.
Keenan, et al. "Clinical factors associated with resistance to microvascular complications in diabetic patients of extreme disease duration" Diabetes Care; Aug. 2007; vol. 30; No. 8; pp. 1995-1997.
Altschul, et al. "Gapped BLAST and PSI-BLAST: a new generation of protein database search programs" Nucleic Acids Research; 1997; vol. 25; No. 17; pp. 3389-3402.

(Continued)

*Primary Examiner* — Julie Ha
*Assistant Examiner* — Kristina M Hellman
(74) *Attorney, Agent, or Firm* — Pierce Atwood LLP; Kevin M. Farrell; David J. Wilson

(57) ABSTRACT

Compositions and methods for diagnosing, predicting risk of and/or treating diabetic nephropathy (DN).

8 Claims, 19 Drawing Sheets

(56) References Cited

OTHER PUBLICATIONS

Simpson "Proteins and Proteomics: A Laboratory Manual" Cold Spring Harbor Laboratory Press; 2002; cover, inside pages and Table of Contents; (3 pages).
Miller "Progress Toward Human Gene Therapy" Blood; Jul. 15, 1990; vol. 76; No. 2; pp. 271-278.
Ausubel, et al. "Transduction of Genes Using Retrovirus Vector" Current Protocols in Molecular Biology; 1992; Supplement 17; Sections 9.10-9.14 (32 pages).
Eglitis, et al. "Gene Expression in Mice After High Efficiency Retroviral-Mediated Gene Transfer" Science; Dec. 20, 1985; vol. 230; pp. 1395-1398.
Berkner "Development of Adenovirus Vectors for the Expression of Heterologous Genes" BioTechniques; 1988; vol. 6; No. 7; pp. 616-629.
Rosenfeld, et al. "Adenovirus-Mediated Transfer of a Recombinant Alpha1-Antitrypsin Gene to the Lung Epithelium in Vivo" Science; Apr. 19, 1991; vol. 252; pp. 431-252.
Rosenfeld, et al. "In Vivo Transfer of the Human Cystic Fibrosis Transmembrane Conductance Regulator Gene to the Airway Epithelium" Cell; Jan. 10, 1992; vol. 68; pp. 143-155.
Muzyczka "Use of Adeno-Associated Virus as a General Transduction Vector for Mammalian Cells" Current Topics in Microbiology and Immunology, 1992; vol. 158; pp. 97-129.
Flotte, et al. "Gene Expression from Adeno-associated Virus Vectors in Airway Epithelial Cells" Am. Journal Respir. Cell Mol. Biol.; 1992; vol. 7; pp. 349-356.
Remington's Pharmaceutical Sciences, 18th Edition; Gennaro Edition; 1990; Chapter 27; pp. 484-494.
Nies, et al. Chapter 3 "Principles of Therapeutics" in Goodman & Gilman's "The Pharmacological Basis of Therapeutics" 9th Edition; 1996; pp. 43-62.
Gao, et al. "Extracellular carbonic anhydrase mediates hemorrhagic retinal and cerebral vascular permeability through prekallikrein activation" Nature Medicine; Feb. 2007; vol. 13; No. 2; pp. 181-188.
Yacovan, et al. "1-(sulfonyl)-5-(arylsulfonyl)indoline as activators of the tumor cell specific M2 isoform of pyruvate kinase" Bioorganic & Medicinal Chemistry Letters; 2012; vol. 22; pp. 6460-6468.
Iori, et al., "Glycolytic enzyme expression and pyruvate kinase activity in cultured fibroblasts from type 1 diabetic patients with and without nephropathy" Biochimica et Biophusica Acta; vol. 1782; 2008; pp. 627-633.
Gupta, et al., "Dominant Negative Mutations Affect Oligomerization of Human Pyruvate Kinase M2 isozyme and Promote Cellular Growth and Polyploidy" Journal Biol Chem.; vol. 285; No. 22; May 28, 2010; pp. 16864-16873.
Trojanowicz, et al. "Proteomic approach reveals novel targets for retinoic acid-mediated therapy of thyroid carcinoma" Molecular and Cellular Endocrinology; 2010; vol. 325; pp. 110-117.
Poon, et al. "Proteomics analysis provides insight into caloric restriction mediated oxidation and expression of brain proteins associated with age-related impaired cellular processes: Mitochondrial dysfunction, glutamate dysregulation and impaired protein synsthesis" Neurobiology of Aging; 2006; vol. 27; pp. 1020-1034.

* cited by examiner

A

C

D

E

A

B

C

A

B

C

A

B

C

PREDICTING AND TREATING DIABETIC COMPLICATIONS

This invention was made with government support under grant number DK053105 awarded by NIH. The government has certain rights in the invention.

TECHNICAL FIELD

This invention relates to compositions and methods for diagnosing or predicting risk of diabetic nephropathy (DN), and to compositions and methods for treating DN.

BACKGROUND

Common complications of diabetes (e.g., long-term diabetes) include DN. Moreover, the majority of diabetics develop DN.

SUMMARY

The present invention is based, at least in part, on the discovery of an association between certain biological factors and the incidence, risk, or development of a microvascular complication, e.g., DN. Accordingly, the present disclosure provides that certain of the factors disclosed herein can be used, e.g., as biomarkers to diagnose predict risk of developing a microvascular complication, e.g., DN. The present disclosure also provides that certain of the factors disclosed herein can be used in the treatment or therapy of a microvascular complication, e.g., DN.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
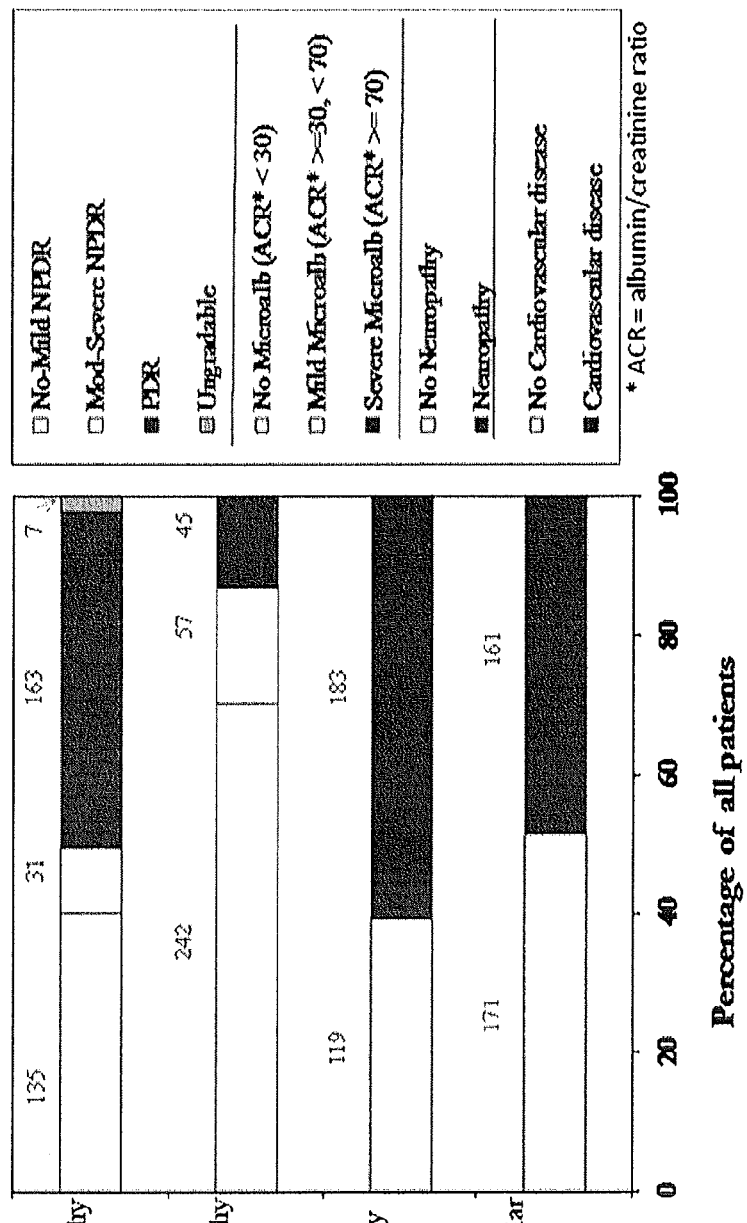
FIG. 1 is a chart showing microvascular and macrovascular complications in the subjects disclosed in Examples.

DN is kidney disease or damage that occurs in diabetics. DN is a major cause of sickness and death in persons with diabetes. It is the leading cause of long-term kidney failure and end-stage kidney disease in the United States, and often leads to the need for dialysis or kidney transplantation.

As further described in the Examples, it has been shown herein that specific factors (e.g., proteins) are expressed at higher levels (e.g., at least 1.5 fold higher level) in type 1 diabetic individuals without a diabetic microvascular complication (DMC), such as diabetic nephropathy (DN), relative to type 1 diabetic individuals DN. Such factors are referred to as "protective factors."

Table 1 provides examples of certain factors that have been identified herein that are expressed at higher levels in type 1 diabetic individuals without DN relative to those with DN. Table 1 provides factors with a statistically significant difference in expression (e.g., at least 1.5 fold) between type 1 diabetic individuals without DN and those with DN (see, Examples), wherein individuals without DN have a higher level of the factors. These factors are DN protective factors.

TABLE 1

DN protective factors, exemplary accession numbers and fold increase in type 1 diabetes individuals without DN relative to those with DN

| Name of Enzymatic and Non-enzymatic proteins from medalist glomeruli | Accession Nos. International Protein Index | Median fold increase | P value* |
|---|---|---|---|
| 1 SOD1—Superoxide dismutase | IPI00218733 [SEQ ID NO: 1] | 2.73 | 0.00252 |
| 2 TPI1$—Triosephosphate isomerase isoform 2 | IPI00465028 [SEQ ID NO: 2] | 2.56 | 0.00352 |
| 3 SORD—Sorbitol dehydrogenase | IPI00216057 [SEQ ID NO: 3] | 5.00 | 0.00313 |
| 4 ALDOA—Aldolase A, fructose-bisphosphate | IPI00796333 [SEQ ID NO: 4] | 3.17 | 0.00468 |
| 5 GAPDH—Glyceraldehyde-3-phosphate dehydrogenase | IPI00219018 [SEQ ID NO: 5] | 2.72 | 0.00666 |
| 6 PKM‡—Pyruvate kinase isozymes M1/M2 | IPI00479186 [SEQ ID NO: 6] | 8.00 | 0.01033 |
| 7 ENO1—Alpha-enolase | IPI00465248 [SEQ ID NO: 7] | 2.70 | 0.00897 |
| 8 FGB—Fibrinogen beta chain | IPI00298497 [SEQ ID NO: 8] | 8.00 | 0.00181 |
| 9 SELENBP1†—Selenium binding protein 1 | IPI00745729 [SEQ ID NO: 9] | 2.7 | 0.00656 |
| 10 PEBP1—Phosphatidylethanolamine-binding protein 1 | IPI00219446 [SEQ ID NO: 10] | 3.2 | 0.00489 |
| 11 CRYL1—Lambda-crystallin homolog | IPI00006443 [SEQ ID NO: 11] | 8.0 | 0.00937 | n of DN class 0 + I = 6
n of DN class IIB + III = 11
*Kruskal-Wallis test
International Protein Index
$IPI00465028 refers to TRIOSEPHOSPHATE ISOMERASE ISOFORM 2, Gene Symbol TPI1, in SRS databse; TPI1 refers to Triosephosphate isomerase 1 in Entrez Gene, also called Triosephosphate isomerase
‡PKM2 is now PKM (Official Gene Symbol) Gene ID: 5315, updated on 15-Jul-2012 in Entrez Gene
†IPI00745729 discontinued in SRS database Methods of Diagnosis and Prognosis The present disclosure provides, inter alia, methods and compositions for diagnosing and predicting risk of developing diabetic microvascular complications (DMCs), e.g., diabetic nephropathy (DN), in a subject. The methods may also be used to determine the effectiveness of a therapy for a DMC or the prognosis of a subject. A method may comprise determining the level (e.g., protein or expression level) or activity of one or more protective or risk factors of a DMC, such as the factors described herein.

The methods include obtaining (or providing) a sample from a subject, e.g., a sample of kidney tissue; plasma or urine, and evaluating the presence and/or level of one or more biomarker described herein (e.g., in Table 1) in the sample, and comparing the presence and/or level with one or more reference values, e.g., a control reference value that represents a normal level of the protein, e.g., a level in an unaffected subject, and/or a disease reference that represents a level of the proteins associated with DN, e.g., a level in a subject having DN or an increased (high) likelihood of developing DN. In a preferred embodiment, the biomarker is a DN protective factor listed in Table 1.

Certain methods may comprise providing a sample from a subject (e.g., a subject having diabetes, e.g., type 1 diabetes), such as plasma, a kidney sample; determining the level of at least one protein (factor) listed in Table 1, in the sample; and determining whether the at least one protein is present in the sample at levels at least 50%, 75% (i.e., 1½ fold), 100% (i.e., 2 fold), 2.5 fold, 3 fold, 4 fold, 5 fold, 10 fold, 15 fold or higher or lower than a control value (e.g., reference level), wherein the control value is, e.g., the level of the factor in a subject having type 1 diabetes for at least 10, 15, 20, 25, or more years and who has not developed a microvascular complication, and wherein a level of one or more proteins of Table 1 that is lower by, e.g., at least 50%, 75% (i.e., 1½ fold), 100% (i.e., 2 fold), 2.5 fold, 3 fold, 4 fold, 5 fold, 10 fold, 15 fold, 20 fold or higher relative to a control value, e.g., the level of the factor in a subject having type 1 diabetes for at least 10, 15, 20, 25, or more years and who has not developed DN, indicates that the subject has or is likely to develop DN.

Certain methods may comprise providing a sample from a subject (e.g., a subject having diabetes, e.g., type 1 diabetes), such as plasma, a kidney sample; determining the level of at least one protein (factor) listed in Table 1, in the sample; and determining whether the at least one protein is present in the sample at levels essentially identical (e.g., at most 10%, 20%, 30%, 40%, 50%, 60%, 70%, 80%, 90% or 100% higher or lower than) a control value (e.g., reference level), wherein the control value is, e.g., the level of the protein in a subject who has developed a microvascular complication (such as DN), wherein a level of one or more proteins of Table 1 that is essentially identical to a control value, e.g., the level of the factor in a subject having DN or a form thereof, indicates that the subject has or is likely to develop DN.

In certain embodiments, the level of a DN protective factor in a subject is compared to both that of a subject who is protected, i.e., has not developed DN after at least 5, 10, 15, 20 or more years of disease, and that of a subject who has developed DN, wherein a level of the DN protective factor in the subject that is significantly closer to that in a subject who is protected than to that in a subject having DN indicates that the subject is likely to be protected from developing DN, whereas a level of the DN protective factor in the subject that is significantly closer to that in a subject who has DN, than to that of a subject that is protected indicates that the subject is likely to develop DN.

A control or reference value may also be a statistically significant value obtained by, e.g., averaging the level of a particular factor present in more than 5, 10, 15, 20, 30, 40, 50, 100 or more individuals with particular characteristic, e.g., diabetes, but no DN.

A control or reference value is generally factor specific, and may be the value of the factor, e.g., a statistically significant value of the factor, in (i) one or more subjects that are protected from a microvascular complication or (ii) one or more subjects that have a microvascular complication. These two types of control or reference values may be referred to "protected control value" (for the value found in protected subjects) and "disease control value" (for the value found in diseases subjects). A reference value may depend on the stage of the microvascular complication. For example, an "SOD1 control value" or "SOD1 reference value" is a control or reference value of SOD1, e.g., the value of SOD1 in one or more subjects that are protected (e.g., a subject having diabetes for over 5, 10, 15, 20, 25, 30, 35, 40, 45 or 50 years and not having developed DN; an "SOD1 protected control value") or the value of SOD1 in one or more subjects that are not protected and have or are likely to develop ON (an "SOD1 disease control value").

In one embodiment, the level of SOD1 (or other marker(s) identified in Table 1) is measured in a subject, e.g., a subject with type 1 or 2 diabetes, to determine the likelihood of the subject from developing a kidney complication, e.g., DN. The level of SOD1 may also be predictive of the effectiveness of a treatment or determining the prognosis of a kidney complication. A method may comprise obtaining a kidney sample (e.g., sample of glomeruli) from a subject and determining the level of SOD1 in the sample. The presence of a lower level (e.g., 1.5 or 2 fold-less) of SOD1 relative to a reference value, e.g., the level of SOD1 in type 1 diabetes subjects who have not developed DN after at least 5, 10, 15, 20 or more years of disease is indicative of the likelihood of the subject to have or to develop DN or a poor prognostic of DN. A method may also comprise comparing the level of SOD1 in a subject to a reference level that is the level of SOD1 that is present in a subject having DN. A subject that is found to have a similar level of SOD1 protein relative to that of a subject having DN is likely to develop a kidney complication, e.g., DN. In certain embodiments, the level of SOD1 in a subject is compared to both that of a subject who is protected, i.e., has not developed DN after at least 5, 10, 15, 20 or more years of disease, and that of a subject who has developed DN, wherein a level of SOD1 in the subject that is significantly closer to that in a subject who is protected than to that in a subject having DN indicates that the subject is likely to be protected from developing DN, whereas a level of SOD1 in the subject that is significantly closer to that in a subject who has DN, than to that of a subject that is protected indicates that the subject is likely to develop DN.

In certain embodiments, an increased level of a protective factor or reduced level of a risk factor is predictive of protection from a particular (or single) microvascular complication, such as DN. In certain embodiments, an increased level of a protective factor may be predictive of protection from more than one microvascular complication, e.g., DN. For example, an increased level of SOD1, e.g., in plasma indicates a reduced risk of a subject to develop DN.

In certain embodiments, a method comprises determining the protein level of at least 2, 3, 4, 5, 6, 7, 8, 9, 10 or more protective or risk factors of Table 1. In certain embodiments, a method comprises determining the protein level of 1-11, 1-10, 1-5, 1-4, 1-3 or 1-2 protective factors set forth in Table 1.

The level or concentration of protective factors may be determined in a tissue sample, such as a kidney sample (e.g., renal glomeruli sample), or bodily fluid sample, e.g., urine, blood, plasma, or intraocular fluid. Protective factors for DN may be preferably measured in a kidney sample, e.g., a renal glomerulus sample.

A "level of a factor" refers to the quantity or concentration of the protein or RNA (e.g., RNA) of the factor, and may also refer to the measurement of any other factor that results in the determination of the level of the factor (e.g., the measurement of the level of a metabolite of an enzyme may be a measurement of the level of the enzyme). Similarly, measurements of upstream products may also be measurements of the level of a factor.

In certain embodiments, the level or concentration of one or more factor is measured in the blood or plasma of a subject. For example, the level of SOD1 may be measured in plasma, wherein an increased (or higher) level of SOD1 in plasma of a first subject relative to that in a second subject indicates that the first subject is less likely than the second subject to develop a kidney problem, such as DN; whereas reduced levels of SOD1 in plasma of a first subject relative to that in a second subject indicates that the first subject is more likely than the second subject to develop a kidney problem, e.g., DN (see Example 3).

A higher level of a protective factor, e.g., SOD1, can also be used as a measure of the success of a treatment. For example, a subject having type 1 diabetes who is responding positively to a diabetic treatment may have a higher level of a protective factor relative to a subject having type 1 diabetes who is not responding to a treatment or to the value of the factor at the beginning of the treatment of the subject. Thus, an increase in the level of a protective factor in a subject with type 1 diabetes who is being treated indicates that the subject responds positively to the treatment.

The presence and/or level of a protein can be evaluated using methods known in the art, e.g., using quantitative immunoassay methods. In some embodiments, high throughput methods, e.g., protein or gene chips as are known in the art (see, e.g., Ch. 12, Genomics, in Griffiths et al., Eds. Modem genetic Analysis, 1999, W. H. Freeman and Company; Ekins and Chu, Trends in Biotechnology, 1999, 17:217-218; MacBeath and Schreiber, Science 2000, 289 (5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of a biomarker listed herein (e.g., in Table 1).

In some embodiments, once it has been determined that a person has DN, or has an increased risk of developing DN, then a treatment, e.g., as known in the art or as described herein, can be administered.

The compositions disclosed herein can include agents that detect or bind (e.g., that detect or bind specifically) to a biomarker described herein (e.g., in Table 1, 3 or 4). Such agents can include, but are not limited to, for example, antibodies, antibody fragments, and peptides. In some instances, the compositions can be in the form of a kit. Such kits can include one or more agents that can detect or bind (e.g., that detect or bind specifically) to one or more biomarkers described herein (e.g., one or more of the biomarkers disclosed in Table 1 and instructions for use.

In certain embodiments, a method comprises determining the level of a protective factor in a subject. The measurement may be performed in the subject, e.g., by imaging, or on a sample obtained from a subject. If the level of the factor is determined in a sample of a subject, a method may comprise first obtaining a sample from a subject, e.g., by using a needle or other apparatus to aspirate a sample. A sample may then be sent to a laboratory for determining the level of the factor, following the doctor's instructions. If the measuring is performed in the subject, the subject may be sent to a particular department in the hospital where they handle such matters, following the doctor's instructions. The level of the factor, as determined in the laboratory or hospital is then sent back to the doctor who had ordered the measurement, or entered into a computer or data system that is accessible to the doctor. The doctor may then compare the value(s) received to reference values, which may, e.g., be present in a computer. For example, the doctor may enter the values into a computer, and the computer performs the comparison with one or more control values. The computer may also provide the conclusion regarding the likelihood of development of a microvascular complication by the subject. The doctor may then discuss the results with the subject, and choose a path forward, e.g., an appropriate treatment; the decision to re-evaluate the level of one or more factors at a later time; or to evaluate other criteria of the subjects, e.g., the presence or absence of certain symptoms.

Methods of Treatment

As used herein, "treatment" means any manner in which one or more of the symptoms of DN are ameliorated or otherwise beneficially altered. As used herein, amelioration of the symptoms of the disorder refers to any lessening, whether permanent or temporary, lasting or transient that can be attributed to or associated with treatment by the compositions and methods of the present invention. With DN, treatment can include lessening of any symptom associated with DN, including, but not limited to, changes in appetite, change in sleep, protein in serum, weakness, and/or nausea.

In some embodiments, the present disclosure provides methods for treating a microvascular complication, e.g., DN, in a subject (e.g., a subject with diabetes (e.g., type 1 and/or type 2 diabetes) by administering to the subject a therapeutically effective amount of one or more (e.g., 1, 2, 3, 4, 5, 6, 7, 8, 9, 10 or more, including all) agents that increase the level or activity of one or more of the DN protective factors disclosed in Table 1. An agent may increase the level or activity of a protective factor or decrease the level or activity of a risk factor by at least 50%, 100% (1-fold), 1½-fold, 2-fold, 3-fold, 4-fold, 5-fold, 10-fold, 15-fold, 20-fold or more. In certain embodiments, a therapeutic method comprises bringing the level or activity of a protective factor essentially to its level or activity in a subject that is protected from the development of a microvascular complication. "Essentially within its level," refers to within less than 5%, 10%, 20%, 30%, 40%, 50%, 60%, 70%, 80%, 90% or 100% of the control value. How close the level or activity can be brought to a control value depends on the particular factor, in particular on how different the level of the factor is in a protected subject versus a diseased subject.

An agent that increases the level or activity of a protective factor may be a small molecule, a protein comprising the protective factor or a biologically active variant (e.g., fragment) thereof, or a nucleic acid encoding a protein comprising the protective factor or a biologically active variant (e.g., fragment) thereof.

Accordingly, the present disclosure includes treatments comprising administering one or more proteins, or nucleic acid(s) encoding the one or more proteins, consisting of, consisting essentially of, or comprising the amino acid sequences, or variants thereof, that are associated with any one or more of the accession numbers of the factors disclosed in Table 1. For example, useful amino acid sequences can have 50%, 60%, 70%, 80%, 85%, 90%, 95%, 98%, 99%, or 100% sequence identity to any one or more of the accession numbers disclosed in Table 1, provided that they retain the necessary biological activity of the factor for its protective characteristics.

The present disclosure also contemplates use of nucleic acid sequences that encode amino acid sequences consisting of, consisting essentially of, or comprising the amino acid sequences associated with any one or more of the accession numbers disclosed in Table 1 or variants thereof. For example, useful nucleic acid sequences can encode an amino acid sequence with 50%, 60%, 70%, 80%, 85%, 90%, 95%, 98%, 99%, or 100% sequence identity to any one or more of the accession numbers disclosed in Table 1.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the (blastp algorithum in) BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul, et al. (Nucleic Acids Res. 25:3389-3402, 1997).

Useful proteins can also comprise amino acid sequences consisting of, consisting essentially of, or comprising the amino acid sequences associated with any one or more of the accession numbers disclosed in Table 1 with one or more (e.g., 1, 2, 3, 4, 5, 6, 7, 8, 9, 10, 20, 30, 40, 50, 60, 70, 80, 90, 100, or any range between any of the afore listed integers, or more than 100) amino acid additions, deletions or substitutions, e.g., conservative amino acid substitutions, provided that the protein retains the necessary biological activity of the factor for its protective characteristics. Conservative amino acid substitutions are known in the art.

In some embodiments, useful proteins can include modified proteins that possess at least a portion of the activity (e.g., biological activity) of the unmodified proteins. For example, modified proteins can retain 50%, 60%, 70%, 80%, 85%, 90%, 95%, 98%, 99%, or 100% of the activity (e.g., biological activity) of the unmodified proteins, e.g., the unmodified version of the amino acid sequences associated with any one or more of the accession numbers disclosed in Table 1.

In some embodiments, useful proteins include proteins that comprise a biologically active fragment of any one or more of the factors disclosed in Table 1.

In some embodiments, treatment of DN or prevention of DN can include administering one or more of the proteins of Table 1 or biologically active variants thereof or nucleic acid encoding such to a subject in need of such treatment or prevention.

Biologically active variants of the proteins of Table 1 also include full length immature and mature forms or fragments thereof that comprise an amino acid sequence that differs from the naturally occurring sequence or fragment thereof in at most 1, 2, 3, 4, 5, 10, 15, 20, 25, 30, 35, 40, 45, 50 or 100 amino acid deletions, additions or substitutions, such as conservative amino acid substitutions. Biologically active variants of the proteins of Table 1 may also include variants that are at least 70%, 80%, 85%, 90%, 95%, 97%, 98% or 99% identical to the full length mature or precursor human PEBP1 protein (or other biomarker identified in this specification) or a fragment thereof.

The present disclosure also includes fusion proteins comprising any one or more amino acid sequence disclosed in Table 1 in combination with a moiety that increases the stability of the fusion protein in vivo (e.g., polyethelene glycol (PEG)) and/or that increases transport of the fusion protein to the therapeutic target (e.g., the kidney).

As further described herein, protein may be administered systemically or locally. For example, a protein for treating or preventing DN, e.g., of the proteins of Table 1 or a biologically active variant thereof, may be administered directly into the kidney or systemically by injection.

Other methods of treatment comprise preventing the degradation of a factor listed in Table 1. Yet other methods include administering an agent that increases the expression of a factor in Table 1. An agent may be a small molecule, e.g., a small molecule that activates the promoter of the factor. In certain embodiments, an agent for treating a subject as described herein is an agent that increases the activity of a factor in Table 1.

The present disclosure also contemplates the use of gene therapy methods, e.g., to administer a nucleic acid encoding one or more of the factors (e.g., protective factors) or nucleic acids inhibiting the expression or activity of a DN risk factor disclosed herein to a subject. For example, nucleic acids encoding a protein disclosed in Table 1, or a variant thereof, or a nucleic acid encoding the protein that increases the expression, level or activity, of one or more of the factors disclosed in Table 1 can be incorporated into a gene construct to be used as a part of a gene therapy protocol.

The invention includes targeted expression vectors for in vivo transfection and expression of a polynucleotide that encodes a polypeptide disclosed in Table 1, or an active fragment thereof, in particular cell types, for cells of the kidney. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology*, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry at al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra).

Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner t al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

In addition to viral transfer methods, such as those illustrated above, non-viral methods can also be employed to cause expression of a nucleic acid compound described herein (e.g., a nucleic acid encoding a polypeptide disclosed in Table 3 or 4, or an active fragment thereof, and/or a nucleic acid that increases the expression and/or activity of a polynucleotide that encodes a polypeptide disclosed in Table 1 in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22):1896-905 (2000); or Tam et al., Gene Ther. 7(21): 1867-74 (2000).

In some embodiments, an agent, e.g., a gene encoding a factor described herein, e.g., a polynucleotide that encodes a polypeptide disclosed in Table 1, or an active fragment thereof, is entrapped in liposomes bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

In some embodiments, the present disclosure includes the use of agonists of any one or more of the factors disclosed in Table 1. In some embodiments, suitable agonists can increase the expression and/or activity of one or more of the factors disclosed in Table 1, e.g., by about 2-fold, 3-fold, 4-fold, 5-fold, or more.

Many of the factors disclosed herein are referenced by the International Protein Index (IPI) number assigned to them. The sequences associated with each of the disclosed IPI numbers are publically available and can be obtained and/or viewed, for example, using the European Institute for Bioinformatics website available at World Wide Web address ebi.ac.uk. Other suitable websites are also known in the art.

Subject Selection

The term "subject" is used throughout the specification to describe an animal, human or non-human, to whom treatment according to the methods of the present invention is provided.

The methods disclosed herein can include selecting a subject for treatment. For example, a subject can be selected if the subject has or is at risk for developing DN, e.g., a subject having diabetes, e.g., type 1 or type 2 diabetes, or a subject who is prediabetic, e.g., having metabolic syndrome, insulin resistance, hyperglycemia, hyperlipidemia or a subject who is overweight or obese, e.g., having a BMI≥25. In some instances, a subject can be selected if the subject has or is at risk for developing type 1 and/or type 2 diabetes. In some instances, a subject can be selected if the subject is taking or will take insulin, e.g., to treat diabetes.

Routes of Administration

One or more (e.g., 1, 2, 3, 4, 5, 6, 7, 8, 9, 10, 11, 12, 13, 14, 15, 16, 17, 18, 19, 20, or more, including all) of the agents, such as factors disclosed herein (e.g., disclosed in Tables 1, 3 and/or 4), can be administered alone or as a pharmaceutical composition (disclosed below) using any mode of administration, e.g., including any mode of administration that results in a therapeutically effective level in the kidney (for DN). In some instances, a therapeutically effective level is an amount or level that results in one or more of the symptoms of DN being ameliorated or otherwise beneficially altered. For the treatment of DN, an exemplary route of administration can include local administration to the kidney. Other exemplary modes of administration suitable for either DN include, but are not limited to, oral, parenteral, inhalation (e.g., as a spray), topical, rectal, nasal, buccal, vaginal, and/or via an implanted reservoir.

The term parenteral as used herein includes subcutaneous, intracutaneous, intravenous, intramuscular, intraarticular, intraarterial, intrasynovial, intrasternal, intrathecal, intralesional and intracranial injection or infusion techniques. Alternatively or in addition, the present invention may be administered according to any of the Food and Drug Administration approved methods, for example, as described in CDER Data Standards Manual, version number 004 (which is available at fda.give/cder/dsm/DRG/drg00301.htm). Where application over a period of time is advisable or desirable, the compositions of the invention can be placed in sustained released formulations (e.g., hydrogels) or implantable devices (e.g., implantable pumps).

Pharmaceutical Compositions

One or more (e.g., 1, 2, 3, 4, 5, 6, 7, 8, 9, 10, or more, including all) of the agents, e.g., factors disclosed herein (e.g., disclosed in Table 1, can be formulated in or as pharmaceutical compositions. Such pharmaceutical compositions can contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

In some cases, pharmaceutical compositions containing one or more factors can be formulated according to the intended method of administration.

Pharmaceutical compositions containing one or more factors can be formulated in a conventional manner using one or more physiologically acceptable carriers or excipients. The nature of the pharmaceutical compositions for administration is dependent on the mode of administration and can readily be determined by one of ordinary skill in the art. In addition, methods for making such formulations are well known and can be found in, for example, Remington's Pharmaceutical Sciences, 18th Ed., Gennaro, ed., Mack Publishing Co., Easton, Pa., 1990. In some embodiments, the pharmaceutical composition is sterile or sterilizable.

Pharmaceutical compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol.

In some embodiments, pharmaceutical compositions can be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the composition may be in powder form for constitution with a suitable vehicle, for example, sterile pyrogen-free water, before use. Agents that enhance delivery into a cell can be used as well, e.g., liposomes or micelles.

In addition to the formulations described previously, the compositions can also be formulated as a depot preparation. Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions can also take the form of tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

The methods herein contemplate administration of an effective amount of compound or compound composition to achieve the desired or stated effect. Toxicity and therapeutic efficacy of the compounds and pharmaceutical compositions described herein can be determined by standard pharmaceutical procedures, using either cells in culture or experimental animals to determine the LD50 (the dose lethal to 50% of the population) and the ED50 (the dose therapeutically effective in 50% of the population). The dose ratio between toxic and therapeutic effects is the therapeutic index and can be expressed as the ratio LD50/ED50. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods described herein, the therapeutically effective dose can be estimated initially from cell culture assays. A dose can be formulated in animal models to achieve a circulating plasma concentration range that includes the IC50 (that is, the concentration of the test compound which achieves a half-maximal inhibition of symptoms) as determined in cell culture. Such information can be used to more accurately determine useful doses in humans.

The formulations and routes of administration can be tailored to the disease or disorder being treated, and for the specific human being treated. A subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

Generally the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: Remington's Pharmaceutical Sciences, 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, In: Goodman & Gilman's "The Pharmacological Basis of Therapeutics", 9th Ed., Hardman et al., eds., McGraw-Hill, New York, N.Y., 1996).

Subject Evaluation

The methods can also include monitoring or evaluating the subject during and after treatment to determine the efficacy of the treatment, and, if necessary, adjusting treatment (e.g., by altering the composition, by increasing the dose of a single administration of the composition, by increasing the number of doses of the composition administered per day, and/or by increasing the number of days the composition is administered) to improve efficacy. Monitoring or evaluating the subject can include identifying a suitable marker of disease prior to commencing treatment and optionally recording the marker, and comparing the identified or recorded marker to the same marker during and/or after treatment. Suitable markers can include one or more symptoms of the subject's disease. Suitable markers also include one or more of the factors described in Table 1. Adjustment of treatment would be recommended where the marker is a symptom of disease and comparison of the marker during or after treatment with the marker prior to treatment revealed either no change in the marker or an increase in the marker. Conversely, adjustment of treatment may not be required using the same markers where an increase in the marker is observed.

EXAMPLES

The invention is further described in the following examples, which do not limit the scope of the invention described in the claims.

Example 1

Identification of Protective DN Factors

Evidence that diabetic pathologies can be halted has been documented by the Joslin 50-Year Medalist Study (Keenan et al., Diabetes Care. 2007 August; 30(8):1995-7. Epub 2007 May 16). Population characteristics for these subjects are shown in Table 2.

TABLE 2

Characteristics of Medalist Study Participants

|  | % (n); mean ± std dev |
|---|---|
| Male (%) | 47.0% (192) |
| HbA1c (%) | 7.3% ± 1.1 |
| Age (years) | 67.2 ± 7.4 |
| Age at diagnosis (years) | 11.0 ± 6.5 |
| Duration (years) | 56.2 ± 5.8 |
| BMI (kg/m$^2$) | 26.0 ± 5.1 |
| C-peptide (nmol/L) | 0.07 ± 0.12 |
| Cholesterol (mmol/L) | 4.2 ± 0.9 |
| HDLc (mmol/L) | 1.6 ± 0.5 |
| LDL (mmol/L) | 2.2 ± 0.6 |
| Triglycerides (mmol/L) | 0.9 ± 0.5 |
| Insulin dose (u/kg) | 0.46 ± 0.2 |
| Family History    Any DM | 29.7 (122) |
|                   T1 DM | 12.9 (53) |
| DR3 | 38.8 (116) |
| DR4 | 52.0 (156) |
| DR3 or DR4 | 93.7 (295) |
| DR3/4 | 39.1 (118) |
| IA2 or GAD | 29.7 (111) |
| IA2 | 14.9 (56) |
| GAD | 18.4 (69) |
| PDR | 55 (163) |
| Microalbuminuria (ACR < 7.91 ) | 13.1 (45) |
| Neuropathy (MNSI > 2) | 60.6 (183) |
| CVD | 48.3 (160) |

This study characterizes a number of individuals collectively referred to herein as 'Medalists' who have lived with for 50 or more years with type 1 diabetes (T1DM) by clinical exam, medical history and extensive chemistries.

A total of 30 kidney samples from the Medalists were analyzed by mass spectrometry as previously described (Gao, et al., J Proteome Res. 2008; 7:2516-25; Gao, et al. Nat Med. 2007; 13:181-8). Using the results from the proteomic analyses and correlated pathology derived from the renal glomeruli, we found that the expression of 11 proteins are significantly (1.5 fold) greater in kidneys without disease (DN class 0-I) vs. those with class IIb and III levels of nephropathy. The proteins are listed in Table 3 (enzymatic proteins) and Table 4 (non-enzymatic proteins).

Complications observed in Medalists are shown in FIG. 1 and a summary of clinical characteristics in Medalists is shown in Table 5. Candidate factors that protect against DN were identified by comparing the levels or expression of factors in individuals with DN and those without DN. Factors with a statistically significant difference in expression between the individuals with DN and those without DN were selected. Further statistical analysis was then applied to select protective factors from the candidate factors. After applying Kruskal-wallis statistical analysis, a total of 11 protective factors (see, Table 1) were identified, as shown in Tables 1, 3 and/or 4. The criteria of the selection for protective factors was p value <0.05, and expression level increased >=1.5 fold in individuals without DN.

The analysis was performed essentially as follows. The protein analysis was done using a label-free quantitative analysis of 1D PAGE-LC/MS/MS-based proteomics. Soluble proteins from kidney tissues of 50-Year Medalists were loaded onto 10%/o acrylamide protein gels for separations in 1-D gel electrophoresis. We loaded 200 µg (micro gram) of protein-prep (isolated by sieving, buffering, centrifuging, etc.) with sample buffer in each sample lane on the gel. Then the gel was stained with Coomassie Blue. Each lane of gel was then cut into 40 slices. The 40 slices were digested in separate tubes by trypsin. These digested protein gel slices were then loaded into an LC machine for the later MS/MS analysis.

The number of peptide hits was obtained from the "MS manager," software previously developed by Benbo Gao (Gao B, et al., Mol Cell Proteomics 2008; 7:2399-2409). MS manager is designed based on the PHP-MySQL-Apache platform. It compiles the search results from SEQUEST and X!Tandem of MS/MS data, and then parses these results into the MySQL database. After applying the algorithm for filtering proteins and combining the IPI identifier, a final report of identified proteins is generated in a table with peptide hit numbers. The results are shown in Tables 1, above, and Tables 3 and 4, below.

The first column in Tables 3 and 4 show the gene symbol, the second columns show the International Protein Index numbers (IPI numbers) of the protective factor proteins. These accession numbers were retrieved from mass spectrometry analysis result, mapped to EMBI-EBI IPI database. The third column shows protein names of DN protective factors and the fourth column shows the gene names. Column five shows the Median fold change in expression of type 1 diabetic individuals without DN compared to those with DN. Column six shows P-value and column seven shows the probable protein function.

Validation of the proteins identified through comparison of those with and without DN will be done using samples of urine, plasma and serum from the Joslin Natural History of Microalbuminuria Studies. The validation study will be a case-control testing the hypothesis of a significantly lower level of the factor of interest being present in fast progressors, defined as those who have had a greater than 7% eGFR loss of per year over a 10 year period within 15 year duration compared to those with chronic kidney disease classifications 1, 2, or 3.

TABLE 3

| Gene Symbol | Accession# | Protein Name | Gene Name | Median fold change | P value* | Function |
|---|---|---|---|---|---|---|
| SOD1 | IPI00218733 | SOD1 Superoxide dismutase | Superoxide dismutase 1, soluble | 2.73 | 0.00252 | SOD1 binds copper and zinc ions and is one of three superoxide dismutases responsible for destroying free superoxide radicals in the body. |
| TPI1$ | IPI00465028 | TRIOSEPHOSPHATE ISOMERASE ISOFORM 2 | Triosephosphate isomerase 1 | 2.56 | 0.00352 | Catalyzes the isomerization of glyceraldehydes 3-phosphate (G3P) and dihydroxy-acetone phosphate (DHAP) in glycolysis and gluconeogenesis. Catalytic activity: D-glyceraldehyde 3-phosphate = glycerone phosphate |
| SORD | IPI00216057 | Sorbitol dehydrogenase | sorbitol dehydrogenase | 5.00 | 0.00313 | Converts sorbitol, the sugar alcohol form of glucose, into fructose without using ATP. Converts sorbitol to fructose. Part of the polyol pathway that plays an important role in sperm physiology. Catalytic activity: L-iditol + NAD(+) = L-sorbose + NADH |
| ALDOA | IPI00796333 | Aldolase A, fructose-bisphosphate | aldolase A, fructose-bisphosphate | 3.17 | 0.00468 | Converts fructose 1,6-bisphosphate (F-1,6-BP) into glyceraldehyde 3-phosphate and dihydroxyacetone phosphate (DHAP) in glycolysis and gluconeogenesis. In addition, may also function as scaffolding protein |
| GAPDH | IPI00219018 | Glyceraldehyde-3-phosphate dehydrogenase | glyceraldehyde-3-phosphate dehydrogenase | 2.72 | 0.00666 | Converts glyceraldehyde 3-phosphate and 2 NAD+ into D-glycerate 1,3-bisphosphate and 2 NADH in glycolysis. Has both glyceraldehyde-3-phosphate dehydrogenase and nitrosylase activities, thereby playing a role in glycolysis and nuclear functions, respectively. |
| PKM‡ | IPI00479186 | Pyruvate kinase isozymes M1/M2 | pyruvate kinase, muscle | 8.00 | 0.01033 | Catalytic activity: ATP + pyruvate = ADP + phosphoenolpyruvate. Glycolytic enzyme that catalyzes the transfer of a phosphoryl group from phosphoenolpyruvate (PEP) to ADP, generating ATP. |
| ENO1 | IPI00465248 | Alpha-enolase | enolase 1, (alpha) | 2.70 | 0.00897 | One of three enolase isoenzymes found in mammals. It functions as a glycolytic enzyme. Catalytic activity: 2-phospho-D-glycerate = phosphoenolpyruvate + H(2)O |

TABLE 4

| Gene Symbol | Accession# | Protein Name | Gene Name | Median fold change | P value* | Function |
|---|---|---|---|---|---|---|
| FGB | IPI00298497 | Fibrinogen beta chain | fibrinogen beta chain | 8.00 | 0.001811937 | Fibrinogen has a double function: yielding monomers that polymerize into fibrin and acting as a cofactor in platelet aggregation |
| SELENBP1$ | IPI00745729 | SELENBP1 54 kDa protein | selenium binding protein 1 | 2.70 | 0.006555802 | Selenium-binding protein which may be involved in the sensing of reactive xenobiotics in the cytoplasm. Maybe involved in intra-Golgi protein transport. |
| PEBP1 | IPI00219446 | Phosphatidyl-ethanolamine-binding protein 1 | phosphatidyl-ethanolamine binding protein 1 | 3.20 | 0.004891312 | Binds ATP, opioids and phosphatidylethanolamine. Inhibits the kinase activity of RAF1 by inhibiting its activation and by dissociating the RAF1/MEK complex and acting as a competitive inhibitor of MEK phosphorylation. (Biocarta:) Signal transduction through IL1R |

TABLE 4-continued

| Gene Symbol | Accession# | Protein Name | Gene Name | Median fold change | P value* | Function |
|---|---|---|---|---|---|---|
| CRYL1 | IPI00006443 | Lambda-crystallin homolog | crystallin, lambda 1 | 8.00 | 0.009373867 | It catalyzes the dehydrogenation of L-gulonate into dehydro-L-gulonate in the uronate cycle. [L-gulonate + NAD(+) = 3-dehydro-L-gulonate + NADH] |

Example 2

Levels of DN Protective Factors Correlate Positively with the GFR

Candidates identified by our proteomic analysis of the kidney are measured in the plasma of normal and type 1 diabetic patients to validate the relationship with protection against DN, and to examine whether there is a temporal relationship with progression of DN.

The biomarkers listed in Tables 1, 3 and 4 were identified as a biomarkers in the kidney. The known functions of the identified biomarkers are given in Tables 3 and 4.

Prophetically, biomarker levels will be measured by ELISA method (or other suitable method) in about 10-50 Medalists and a positive correlation will be observed between the level of the identified biomarkers and estimated glomerular filtration rate (GFR) calculated by cystatin C. The estimation of GFR by cystatin C is known to those of ordinary skill in the art.

Further, Western Blot will confirm that protein levels of the biomarkers identified in this specification are significantly higher (via statistical analysis) in kidney of Medalists without DN than from Medalists with DN. Cystatin C protein levels will show a similar trend.

Example 3

Identified Biomarkers Protect Cells from High Glucose Exposure

This Example prophetically describes that the biomarkers identified in this specification protect endothelial cells from being activated by high glucose exposure, as shown in an endothelial migration assay.

Human SOD1 (or other biomarker identified herein), for example, will be prepared by transfecting a suitable expression vector (such as Origene (RC08063) into suitable host cells (such as HEK 293 cells) using, for example, Fugene HD (Promega). The cells will then be lysed and target protein will be bound to, for example, M2 resin (Sigma, Aldrich) and eluted using, for example, 1XFlag peptide (Sigma) following the manufacturer's instructions. The purified peptide will be confirmed by immunoblotting against the DDK tag.

The migration assays will be performed as follows: bovine retinal endothelial cells (BREC) will be isolated as previously described (King, et al., *J Clin Invest.* 1983; 71(4):974-979). $3 \times 10^4$ per well will be plated in a 24 well plate. The following day, a scratch will be made, the cells rinsed off with saline to remove floating cells, and incubated with different conditions (low glucose=5.6 mM, high glucose=25.6 mM D-glucose, Vehicle=TBS buffer, RBP3=1: 100 dilution). The width of this gap will be measured at 0 and 4 hours in the corresponding conditions, two pictures of each gap will be taken at each time point and the average was used. Four wells will be plated for each condition. Statistics will be done with excel (student t-test).

The results will show that the biomarkers of the present invention will prevent the endothelial cells from migrating in response to the high glucose concentration, thereby indicating that the biomarkers of the present invention will protect endothelial cells from the toxic effects of a high glucose environment.

Example 4

Pyruvate Kinase M2 (PKM2) and its Glucose Metabolism Pathways are Shown to be Protective of Diabetic Nephrology This Example shows that there was a significant deviation in the prevalence of diabetic nephropathy than the general type 1 diabetic population, specifically glomerular disease among 50-Year Medalists not explained by standard risk factors (e.g., elevated HbA1c, duration). The prevalence of kidney disease is much lower in the Medalists than general type 1 diabetic patients. In addition, the kidney disease in the Medalists did not correlate with HbA1c. To explore the causes post-mortem specimens of kidneys were procured with consent from affected and unaffected individuals who were well-characterize pre-mortem. These tissues were then in part characterized histologically and separated out for proteomic studies. Proteomic studies identified several proteins on a significant level that were differentially up-regulated in those protected from renal diseases and found to be associated with glucose metabolism. The variance in the expression of molecules involved in this pathway was confirmed through end products of metabolism in the urine and plasma in specimens from individuals who donated the post-mortem specimens and other individuals for whom post-mortem samples were not available. Through proteomic and metabolomic analysis, PKM was shown to be one key protein that was consistently elevated which could regulate glucose metabolism through either glycolysis or mitochondrial respiration as has been shown in cancer cells.

Kidneys Collection and Tissues Extractions. Kidneys were procured post-mortem from Joslin Medalists who had consented to participation in the study (Table 5). After the kidneys were harvested they were preserved on ice and delivered to the Joslin Diabetes Center. The kidney was sectioned and a portion was prepared for pathological classification and glomeruli and tubules were isolated from the remaining.

Proteomics Analysis (Mass Spectrometry) on Collected Kidney Tissues. Protein was extracted from collected glomeruli by procedures known to one of ordinary skill in the art. These protein samples were analyzed using mass spectrometry by procedures known to one of ordinary skill in the art. Patients were classified by a trained renal pathologist into DN class as described by Tervaert, et al. (Cohen Tervaert, T W, et al. Pathologic Classification of Diabetic Nephropathy;

J Am Soc Nephrol 21: 556-563, 2010). Those in classes 0-I (unaffected n=6) were compared to those in class IIb-IV (n=13) were placed in the affected group. A non-parametric two-way independent test (Kruskal-Wallis statistic) due to small sample size was used for comparison to determine what peptides were statistically higher among those protected. Table 6 lists the proteins in order of p-value and secondarily by fold change up-regulated in the unaffected compared to affected showing a significant number of glucose metabolism proteins (asterisk) are up-regulated in the protected group. Although the present invention is not limited by theory, we hypothesize that the protected medalists were ameliorate the deleterious effects of hyperglycemia by efficiently metabolizing glucose by either one or multiple pathways.

Metabolomics Analysis in Plasma and Urine in Joslin Medalists. Metabolomic analyses were also performed in 29 Medalist plasma samples and 28 urine samples divided into either a protected or risk groups. Criteria for this grouping were based on elevated HbA1c in the presence of high estimated glomerular filtration rate (marker of good renal function) and/or low DN class (0-1) when available for the protected group (n=13), and a low HbA1c with a low eGFR and/or high DN class (IIb-III) when available (n=16). Table 7 shows the metabolites which were significantly increased in the risk group (p>0.05).

Figure 2:
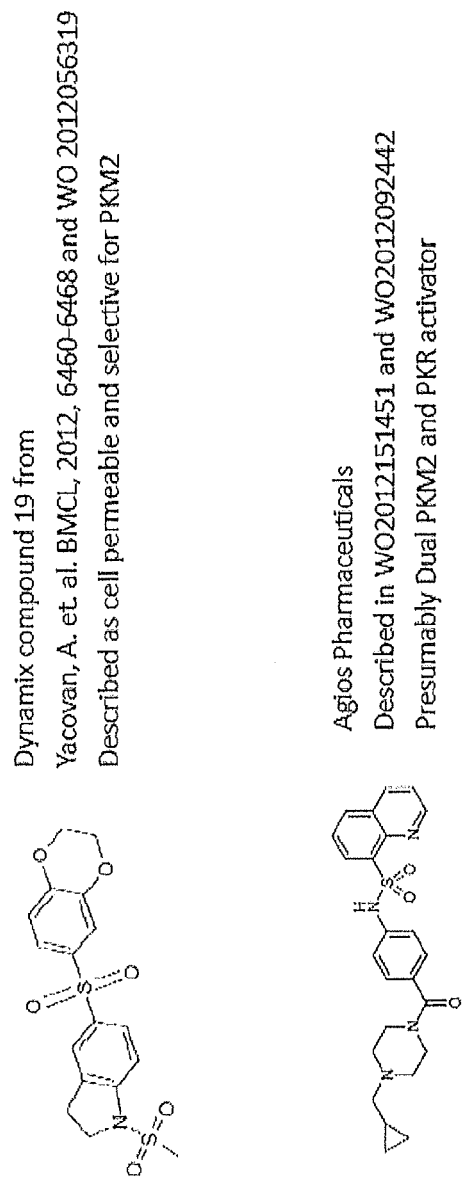
FIG. 2 shows the structures of the Agios and Dynamix compounds used in Example 4.
Figure 7:
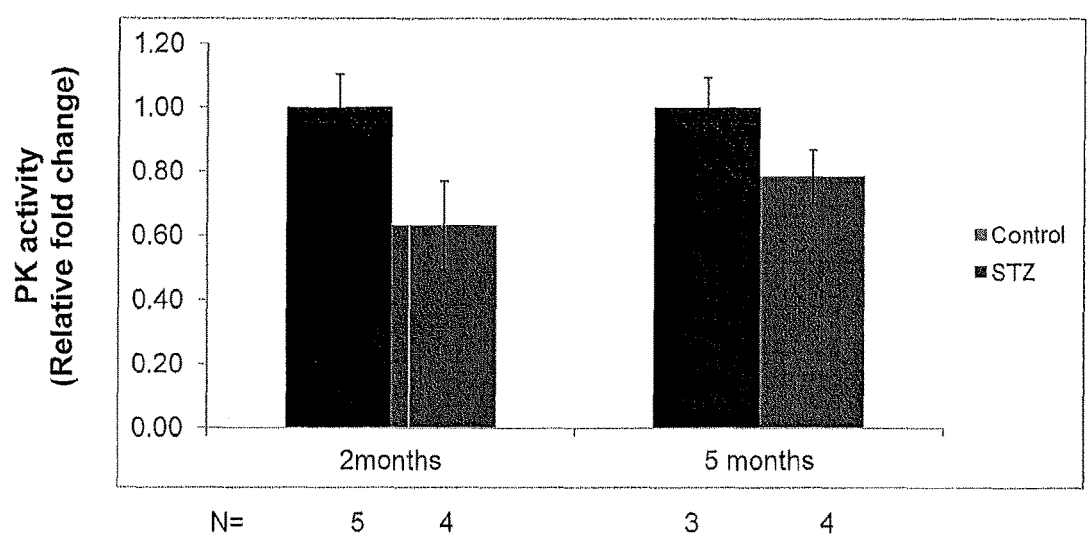
FIG. 7 shows PK activity in the glomeruli from diabetic DBA mice. DBA mice were made diabetic by STZ for 2 and 5 months. Glomeruli were isolated using magnetic beads method and PK activities were measured.

The highlighted metabolites of this group, all either directly or indirectly relate to glycolysis, demonstrate a strong significant change in markers of glycolysis pathways among those protected from glomerular disease. The metabolites which are intermediates of glycolysis F16DP/F26DP/G16DP were found in the plasma. Alpha-glycerophosphate is a product of glycerol metabolism which can be converted to DHAP as a participant in glycolysis. Glucuronate is part of an alternate glucose metabolism pathway (called the glucuronate pathway) that uses 5% of all the body's glucose supply, and ultimately leads to xylitol and vitamin C production. As confirmation of the reliability of the assay and analysis, sorbitol, known to increase in diabetic patients, was found. We plan to study the effect of PKM agonist, such as Agios compound (see, FIG. 2 for the chemical structures of two exemplary compounds from Agios and Dynamix), thieno[3,2-b]pyrrole[3,2-d]pyridazinone, on the development of renal glomerular pathologies in STZ-induced diabetic mice (DBA or C57/BC6). One exemplary method for assessing whether PKM activators are increasing PKM in the renal glomeruli is to measure changes in the serum metabolites which reflect the changes of glycolite products when PKM is activated. The profiles of these glucose metabolites are shown in FIG. 7.

Glucose Metabolism Pathways in the Protected Medalists. Combined proteomic data (Table 6) and metabolomics data (Table 7) show several glucose metabolism pathways are significantly up-regulated in the protected group compared to the affected.

Figure 3:
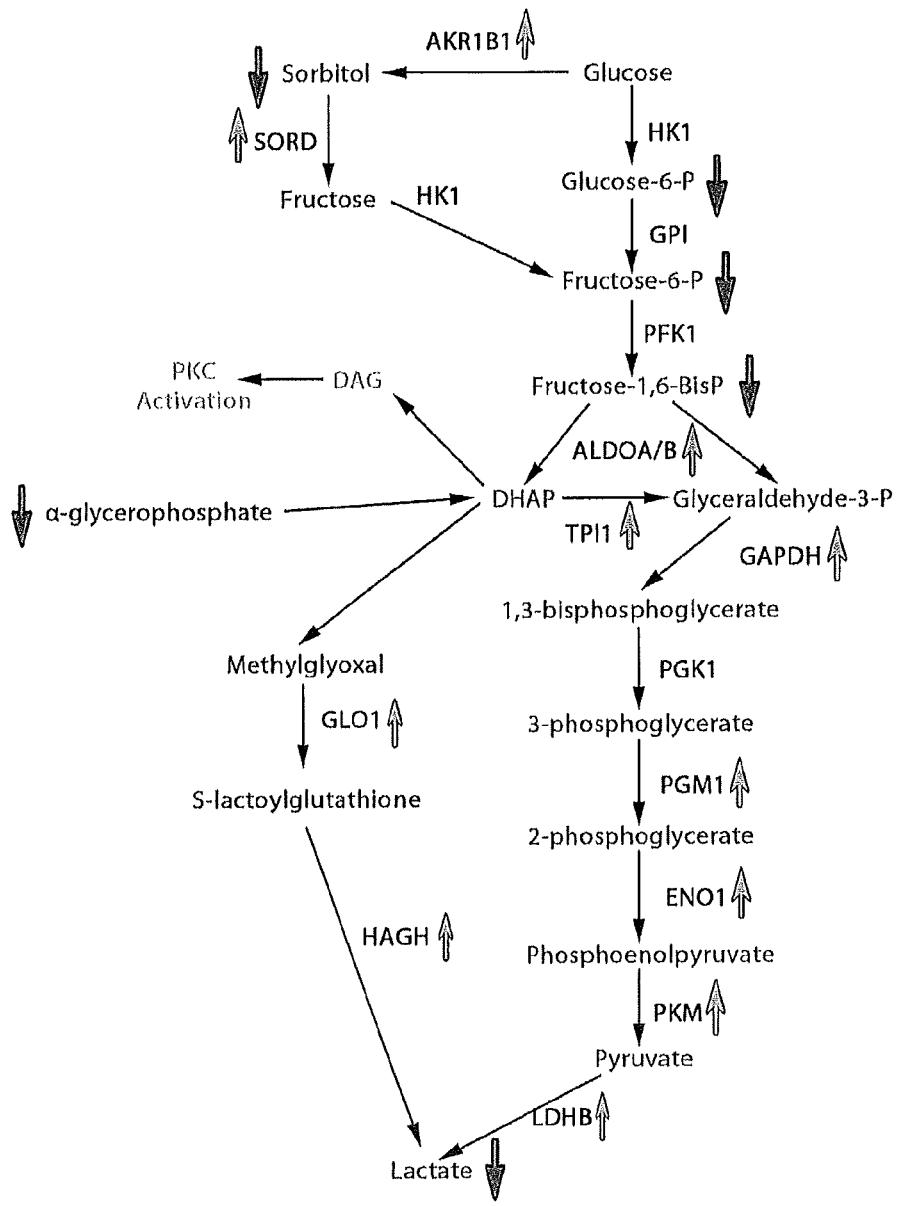
FIG. 3 shows a schematic of glucose metabolism pathways combining proteomic and metabolomics data marking those proteins up-regulated in protected Medalist. Up arrows indicate those proteins are up-regulated in protected medalist glomeruli from proteomic data. Down arrows indicate those metabolites down-regulated in protected from plasma metabolomics data.

Glycolysis related metabolism is where the largest changes are seen between the a protected and affected groups. Of the ten enzymes involved in converting glucose to pyruvate, six were significant or close to significant in proteomic analysis (FIG. 3). Up arrows indicate those proteins are up-regulated in protected medalist glomeruli from proteomic data. Down arrows indicate those metabolites down-regulated in protected from plasma metabolomics data. These enzymes all appear to catalyze the later steps of glycolysis. Furthermore, metabolomic data revealed that glucose-6-phosphate, fructose-6-phosphate, and fructose-1,6-bisphosphate, three metabolites at the beginning steps of glycolysis all decreased in protected medalists. Taken together, renal pathology may result from blockage glycolysis' final steps. Heiden, et al., and Cantley, et al., have shown that pyruvate kinase is the key metabolic gate between aerobic glycolysis and mitochondrial respiration in cancer cells and, as a result, PKM was the focus of this work.

Figure 4:
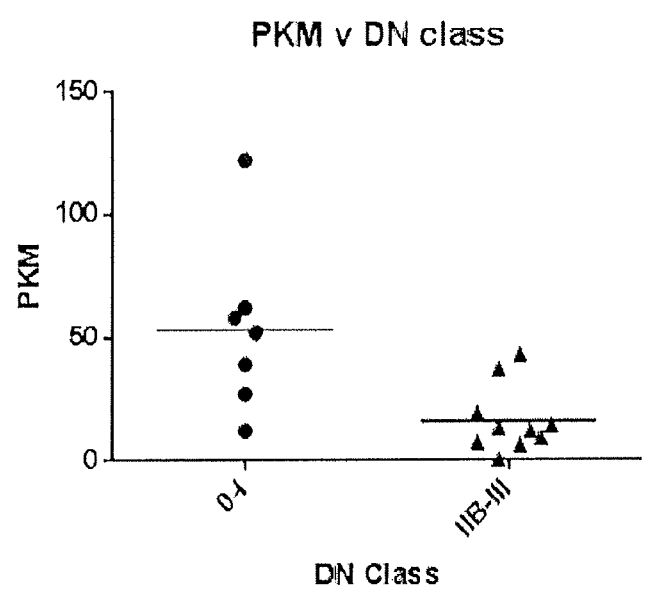
FIG. 4 shows (A) Number of peptides identified for PKM in medalist glomeruli vs DN class, (B) PKM2 and PKM1 protein by western blotting in medalist glomeruli, (C) PKM2 and (D) PKM1 protein levels normalized to actin by western blotting in medalist glomeruli and (E) PKM2 activity in medalist glomeruli.
Figure 4:
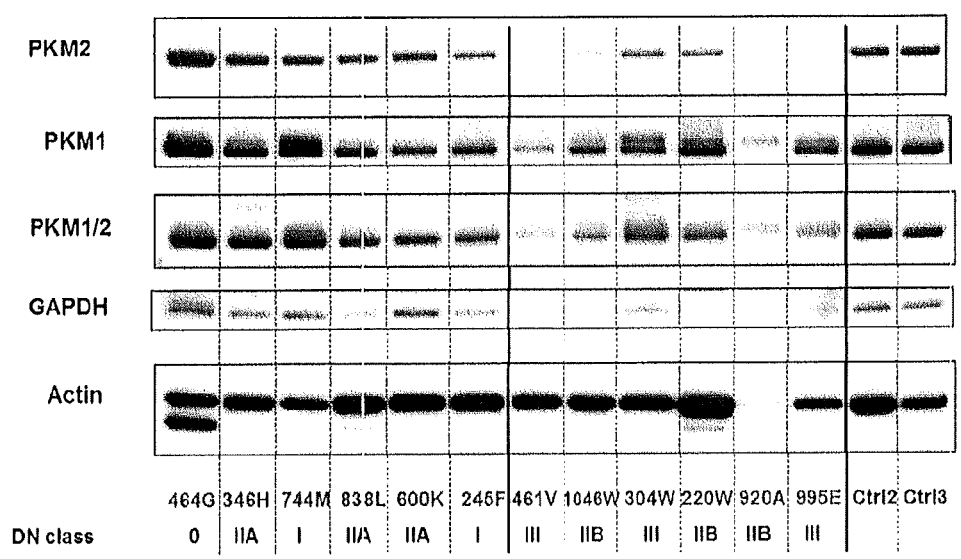
Figure 4:
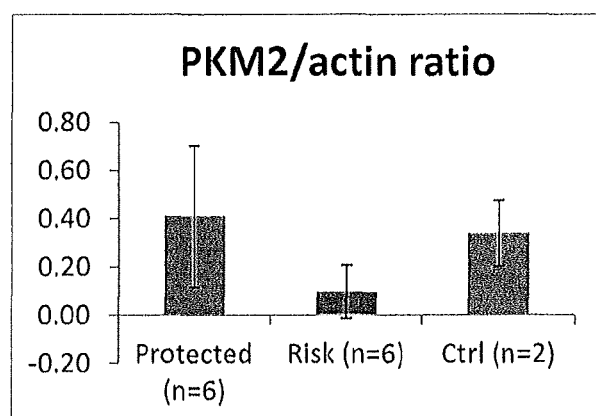
Figure 4:
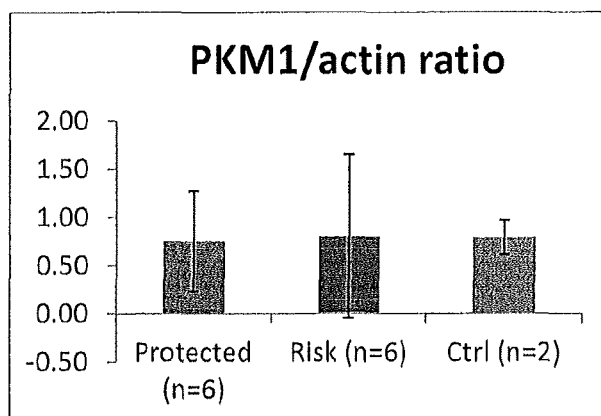
Figure 4:
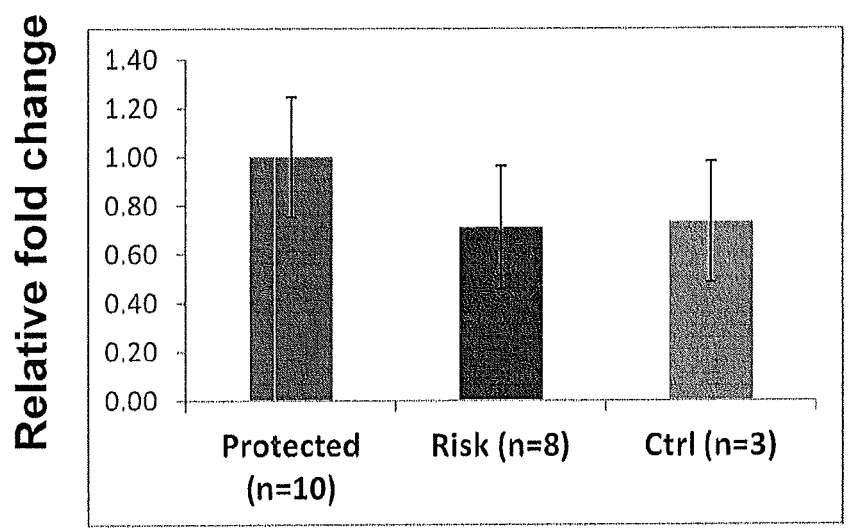

PKM peptide number from proteomic analysis of glomeruli medalist kidneys correlates well with kidney pathology (DN classification) (FIG. 4A), confirmed by Western blotting (blot in FIG. 4B, levels normalized to actin in FIGS. 4C and 4D). Activity levels of pyruvate kinase activity as a marker of disease status is demonstrated in FIG. 4E.

Figure 5:
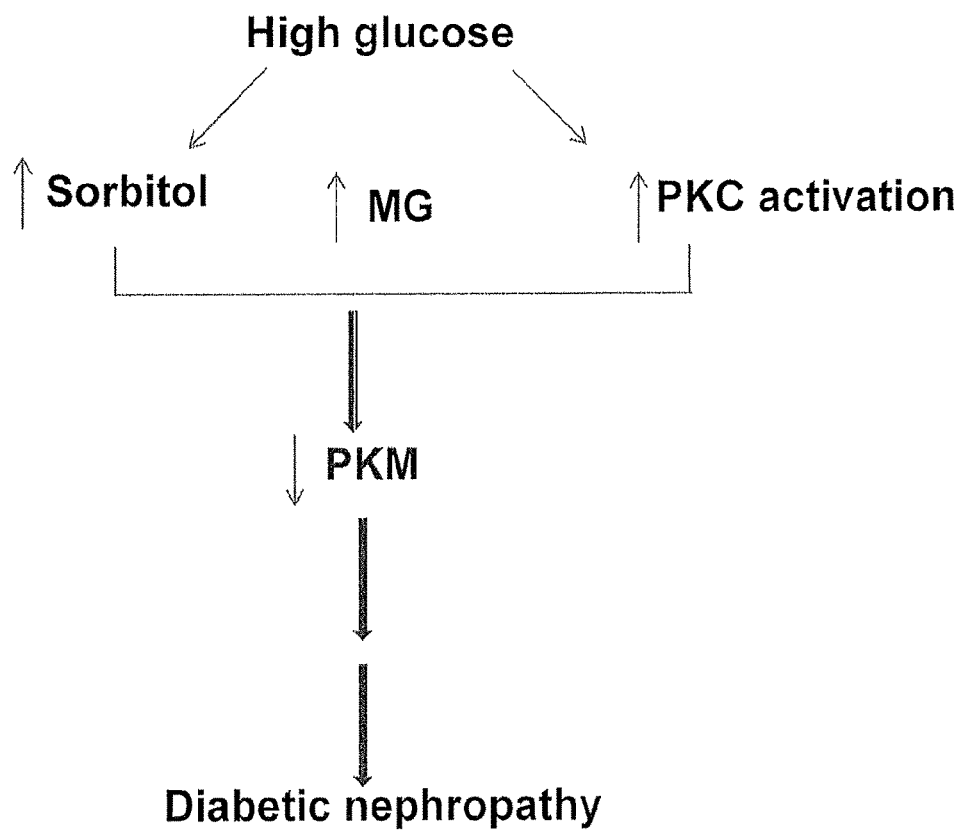
FIG. 5 shows (A) a schema of the hypothesis of the present invention. Although the present invention is not limited by theory, it is hypothesized that decreased PKM level causes metabolites built up such as sorbitol, methylglyoxal (MG) and DAG leading to PKC activation. These abnormalities of glucose metabolism pathways can also lead to ROS accumulation and diabetic nephropathy. (B) Methylgyoxal levels by estimated glomerular filtration levels of 50-Year Medalists. (C) Methylgyoxal levels by Pyruvate Kinase Levels of 50-Year Medalists.
Figure 5:
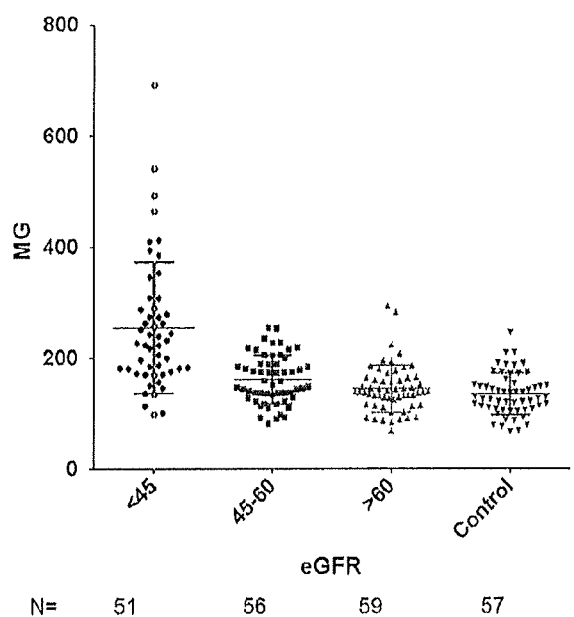
Figure 5:
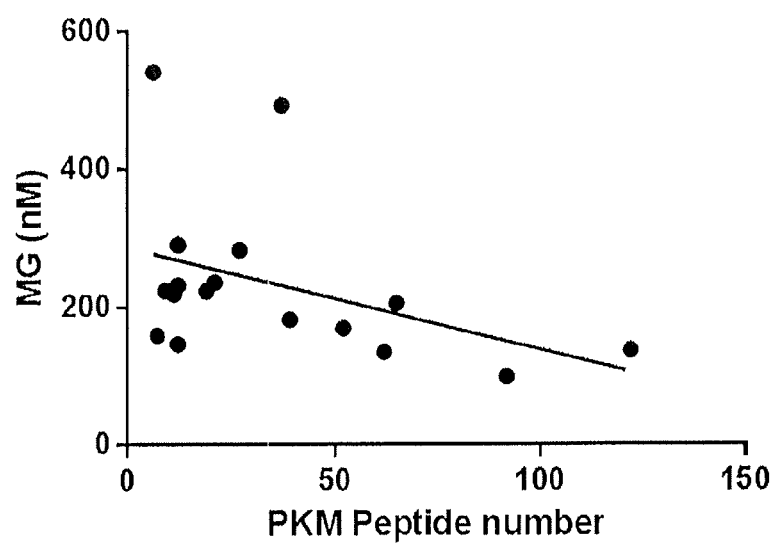

Methylglyoxal (MG) is a highly cytotoxic metabolite that has been implicated in the progression of diabetic kidney disease (Brownlee, Nature 2001). FIG. 5A shows a schematic representation of the hypothesis of the present invention. Although the present invention is not limited by theory, it is hypothesized that decreased PKM level causes metabolites built up such as sorbitol, methylglyoxal (MG) and PKC activation. Plasma MG from Medalists and control (non-diabetic patients) was measured. FIGS. 5B and 5C demonstrate the negative linear association of MG levels between estimated glomerular filtration rates (CKD-EPI formula) as a marker of kidney function and MG and PKM peptide number.

Figure 6:
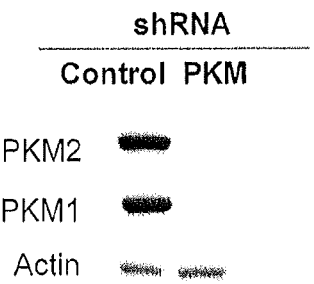
FIG. 6 shows that PKM knockdown in mouse podocytes are more susceptible to apoptosis when exposed to high glucose levels. (A) shows reduction of PKM by shRNA. (B) shows decrease in PKM activity in shRNA PKM treated cells. (C) shows the relative fold change in apoptosis between a=HG+control shRNA vs LG+control shRNA, p=0.0004; b=LG+PKM shRNA vs LG+control shRNA, p=0.0123 and; C=HG+PKM shRNA vs LG+control shRNA, p=0.0069.
Figure 6:
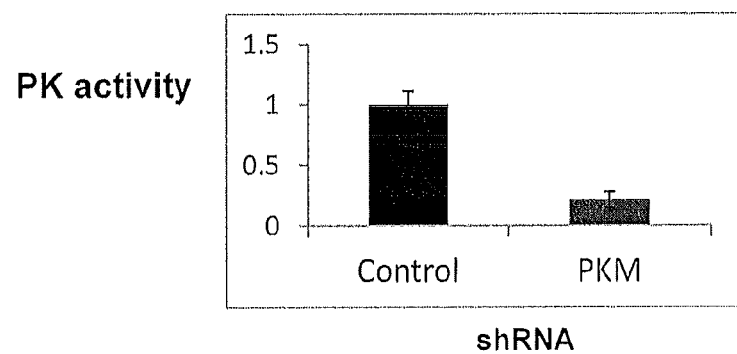
Figure 6:
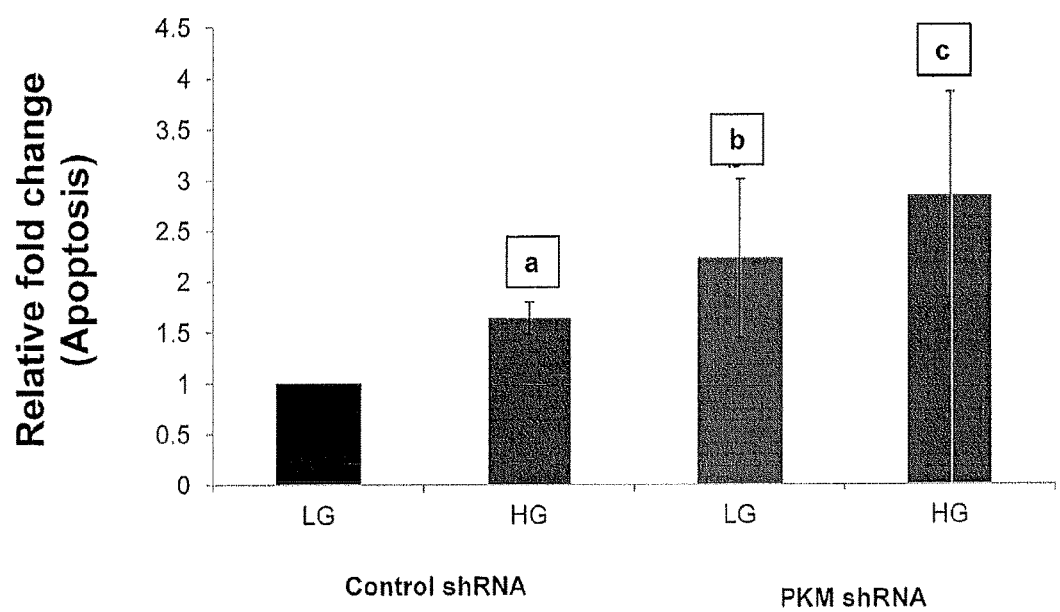

In Vitro Experiment to Confirm In Vivo Findings. In a podocyte cell lines from C57 and DBA PKM2's role was confirmed cell culture. PKM knockdown mouse podocytes (made by techniques known to those of skill in the art) are more susceptible to apoptosis by high glucose. The PKM gene was knocked down (both PKM1 and PKM2) using shRNA in mouse podocytes. FIG. 6A shows inhibition by shRNA. FIG. 6B shows a decrease in PKM activity in shRNA inhibited cells. FIG. 6C shows the relative fold change in apoptosis between a=HG+control shRNA vs LG+control shRNA, p=0.0004; b=LG+PKM shRNA vs LG+control shRNA, p=0.0123 and; C=HG+PKM shRNA vs LG+control shRNA, p=0.0069. PKM2 increased in response to high glucose (LG: 5 mM glucose, HG: 25 mM glucose)

In Vivo Experiments in Murine Model Systems. PK activity in the glomeruli was measured in diabetic DBA mice. DBA mice were induced diabetic by Streptozocin (STZ) for 2 and 5 months using IP injection of 50 mg/kg body weight each day for 5 days. Glomeruli were isolated using magnetic beads method and PK activities were measured by standard methods known o those of ordinary skill in the art. The data in FIG. 7 show that STZ is effective in reducing PK activity.

Figure 8:
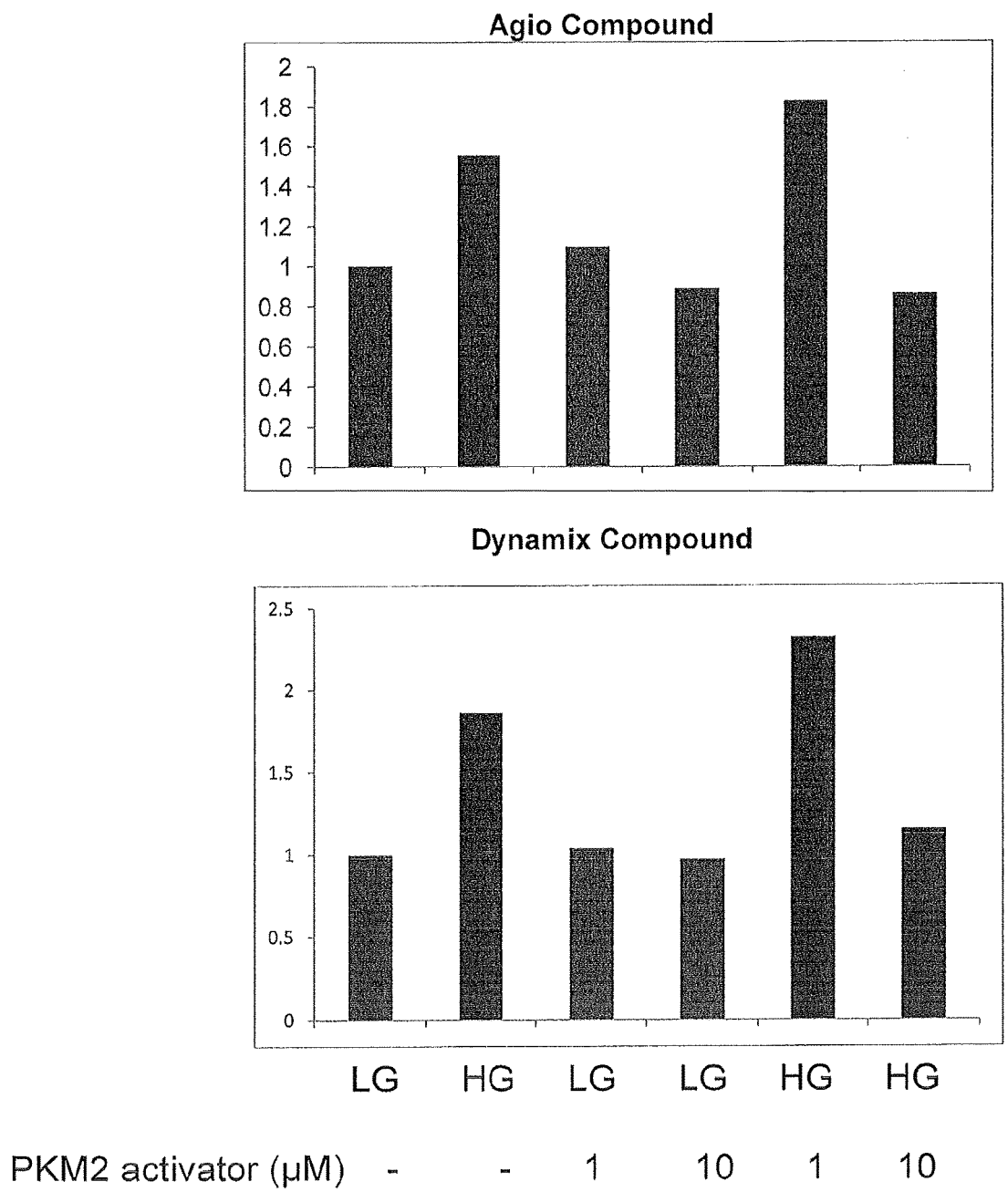
FIG. 8 shows the amount of apoptosis is PKM2 activators dose dependent. Y axis is "Relative Fold Change." (A) Mouse podocytes were treated with low glucose (LG) (5.6 mM), high glucose (HG) (25 mM) −/+PKM2 activators 1 and 10 uM for 72 hrs. Levels of apoptosis were measured. (B) PKM2 activators protect podocytes from apoptosis by high glucose. Mouse podocytes were treated with low glucose (LG), high glucose (HG) −/+10 uM PKM2 activators for 72 hrs. In a separate set of experiments cells were treated with HG for 24 hrs and PKM2 activators were added. Apoptosis were measured. a=HG vs LG: P<0.005; b=HG+Agio (72 hrs) vs. HG: P<0.005; c=HG+Agio (first 24 hrs HG without Agio: final 48 hrs HG+Agio) vs. HG: P<0.005; d=HG+Dyn (72 hrs) vs. HG: P<0.05; e=HG+Dyn (first 24 hrs HG without Dyn; final 48 hrs HG+Dyn) vs. HG: P<0.005.
Figure 8:
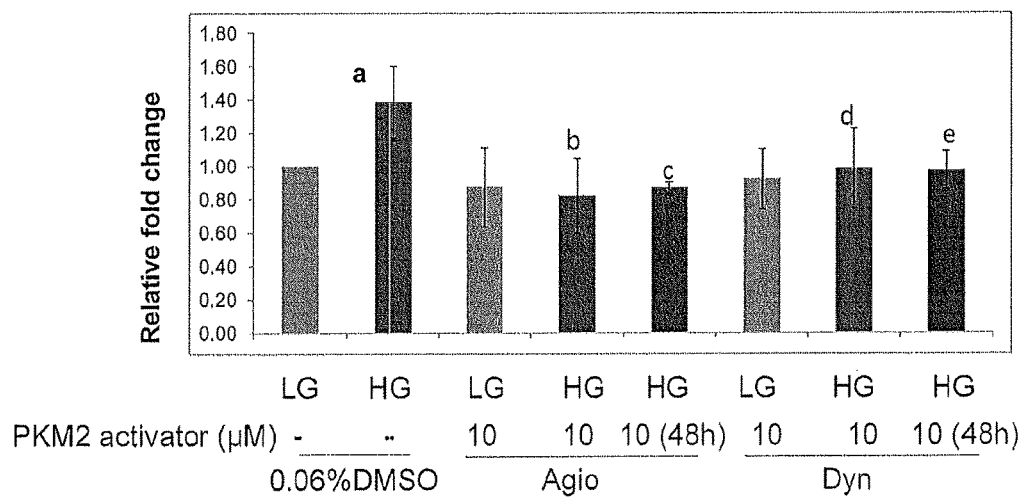

PKM Activators Confirm Protective Effect of PKM. FIG. 8 shows apoptosis is PKM2 activators dose dependent. Y axis is "Relative Fold Change." Agio compound is from Agios Pharmeceuticals (Cambridge, Mass.) and described in International Patent Publication Nos. WO 2012/151451 and WO 2012/092442 (both which are incorporated herein in their entirety). As a dual PKM2 and PKR activator. Dynamix is from Dynamix Pharmaceuticals (Rehovot, Ill.) compound 19 is described in Yacovan, et al., BMCL, 2012, pages 6460-6468 (as known to one of ordinary skill in the art) and in International Patent Publication No. WO 2012/056319 (which is incorporated herein in its entirety) as being cell permeable and selective for PKM2. Mouse podocytes were treated with low glucose (LG), high glucose (HG) −/+PKM2 activators 1 and 10 uM for 72 hrs. Apoptosis were measured (FIG. 8A). FIG. 8B shows that PKM2 activators protect podocytes from apoptosis by high glucose. Mouse podocytes were treated with low glucose (LG), high glucose (HG) −/+10 uM PKM2 activators for 72 hrs. Another set of experiment were treated with HG for 24 hrs and PKM2 activators were added as describe below. Apoptosis were measured. a=HG vs LG: P<0.005; b=HG+Agio (72 hrs) vs. HG: P<0.005; c=HG+Agio (first 24 hrs HG without Agio: final 48 hrs HG+Agio) vs. HG: P<0.005; d=HG+Dyn (72 hrs) vs. HG: P<0.05; e=HG+Dyn (first 24 hrs HG without Dyn; final 48 hrs HG+Dyn) vs. HG: P<0.005.

Figure 9:
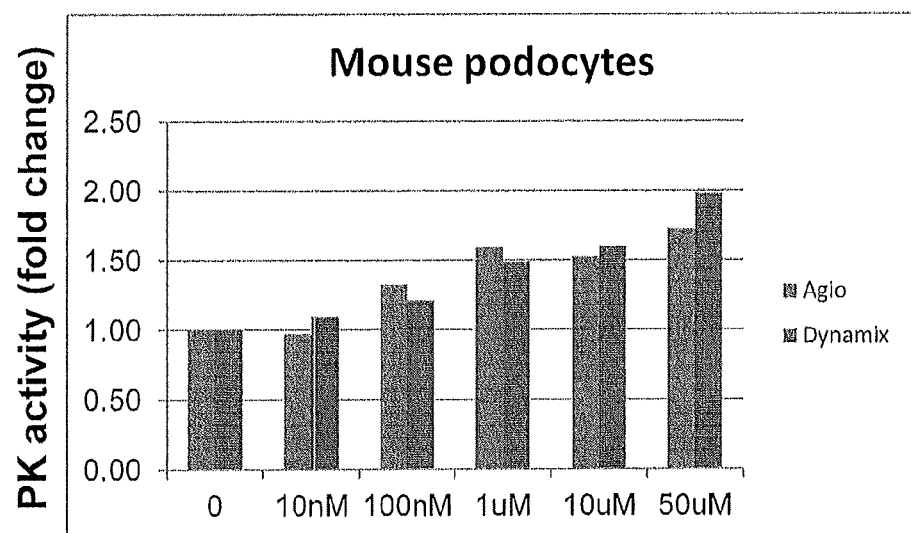
FIG. 9 shows that PKM2 activators protect mouse podocytes from apoptosis. PKM2 activators doses: (A) Mouse podocytes; (B) bovine retinal endothelial cells and (C) mesangial cells (MMC) were treated with 0.01, 1, 10 and 50 uM PKM2 activators (Agio and Dynamix) for 6 hrs. PK activities were measured. N=1.
Figure 9:
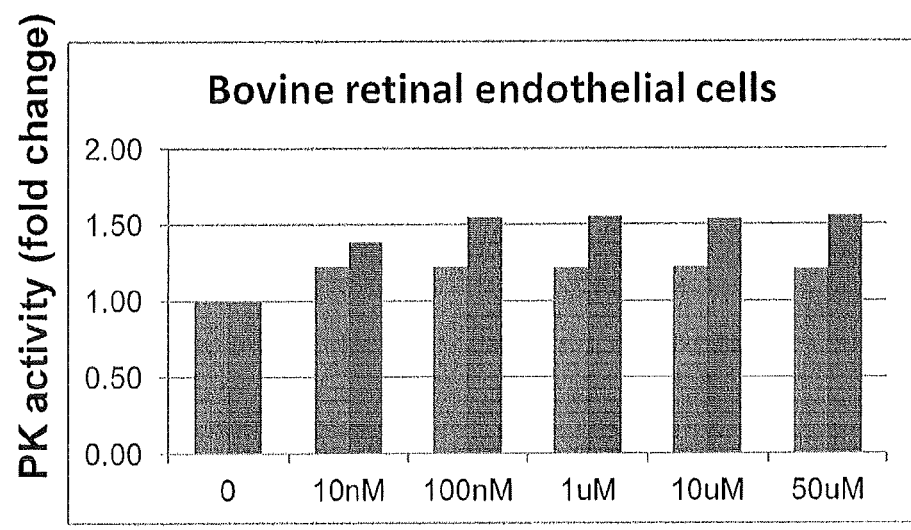
Figure 9:
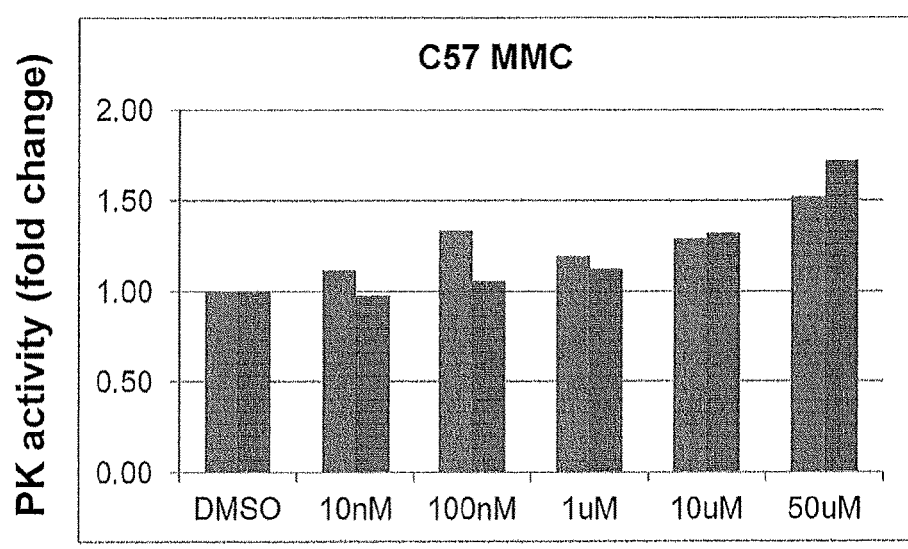

PKM2 activators protect mouse podocytes from apoptosis. FIG. 9 shows different doses of PKM2 activators: (A) Mouse podocytes; (B) bovine retinal endothelial cells and (C) mesangial cells (MMC) were treated with 10, 100 nM, 1, 10 and 50 uM PKM2 activators (Agio and Dynamix) for 6 hrs. PK activities were measured. N=1. Left hand columns of FIG. 8 (A-C) are the Agio compound; right hand columns are the Dynamix compound.

Figure 10:
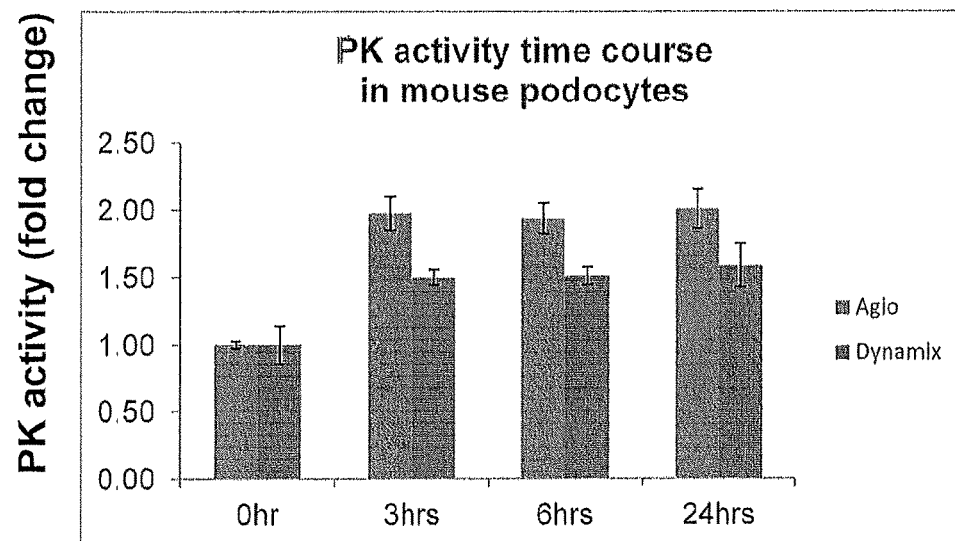
FIG. 10 shows time course of PKM activator actions. (A) Mouse podocytes, (B) bovine retinal endothelial cells and (C) mesangial cells (MMC) were treated with 10 uM PKM2 activators (Agios and Dynamix) for 0, 3, 6 and 24 hrs. PK activities were measured. Agio; N=1; Dynamix; N=2.
Figure 10:
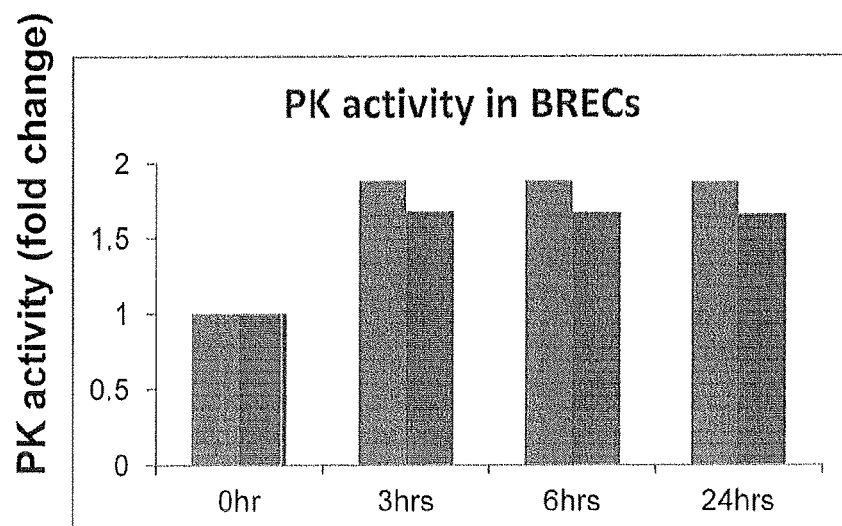
Figure 10:
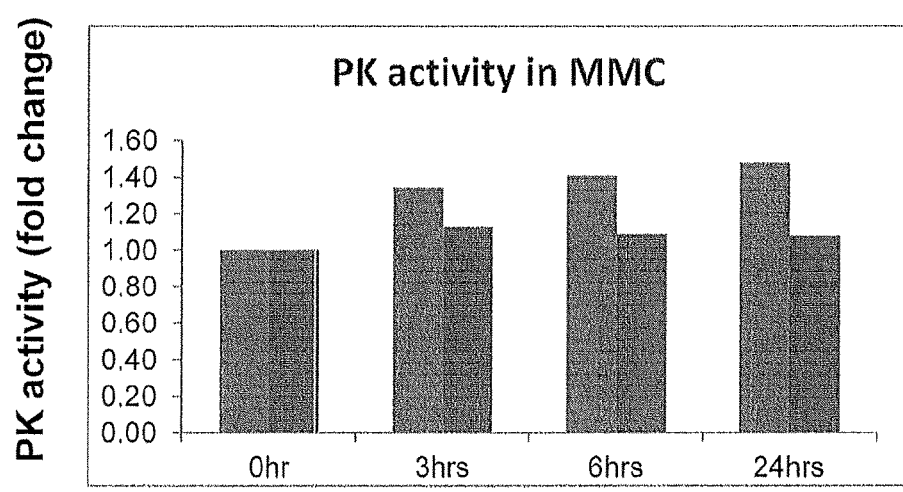

The effect of PKM2 activators in a time course is shown in FIG. 10. (A) Mouse podocytes, (B) bovine retinal endothelial cells and (C) mesangial cells (MMC) were treated with 10 uM PKM2 activators (Agio and Dynamix) for 0, 3, 6 and 24 hrs. PK activities were measured. Agio; N=1; Dynamix; N=2. Left hand columns of FIGS. 10 (A-C) are the Agio compound; right hand columns are the Dynamix compound.

TABLE 5

Traits of Medalists by DN class from whom kidneys have been procured

| DN Class | A1c | Dur | Age | PDR | HTN | ACR | eGFR | Cystatin C | IFTA | GS | GBM | ME |
|---|---|---|---|---|---|---|---|---|---|---|---|---|
| 0 | 7.7 | 76 | 81 | No/mild | No | — | 59.7 | 0.95 | 1 | 12.1 | 345.7 | Mild |
| 0 | 5.7 | 57 | 72 | QPDR | No | 23.9 | 34.5 | 1.18 | 1 | 18.7 | 303 | Mild |
| I | 6.7 | 57 | 80 | No/mild | Yes | 5.4 | 42.7 | 1.76 | 1 | 22.5 | 452.2 | None |
| I | 6.6 | 75 | 79 | QPDR | Yes | 30 | 39.8 | 1.74 | 1 | 18.5 | 492.6 | None |
| I | 6.9 | 55 | 79 | QPDR | Yes | 4.6 | 81.5 | 0.85 | 1 | 5 | — | None |
| I | 8 | 53 | 57 | QPDR | No | 7.4 | 94.4 | 0.75 | 1 | 7 | 480.1 | Mild |
| IIA | 8.2 | 58 | 64 | QPDR | HTN | — | 15.2 | 0.89 | 2 | 22.5 | — | Mild |
| IIA | 7.2 | 84 | 88 | QPDR | Yes | 0 | 37.9 | 1.45 | 3 | 58 | — | Mild |
| IIA | 7.3 | 66 | 73 | QPDR | Yes | 53.6 | 44.3 | 1.21 | 2 | 29.9 | 424.2 | Mild |
| IIA | 6.1 | 62 | 63 | QPDR | Yes | 7.8 | 34 | 1.34 | 1 | 36.5 | — | Mod |
| IIA | 5.6 | 52 | 59 | No/mild | No | 23.4 | 80.9 | 0.96 | 1 | 2.6 | 442.7 | None |
| IIA | 7.2 | 75 | 84 | No/mild | Yes | 0.21 | 46.1 | 1.08 | 2 | 40.1 | — | Mild |
| IIA | 6.6 | 54 | 81 | QPDR | Yes | 13.3 | 69.8 | 0.82 | 2 | 14.1 | 435.6 | Mild |
| IIA | 7.4 | 60 | 77 | No/mild | Yes | 16.2 | 61.9 | 0.73 | 2 | 8.3 | 471.6 | Mod |
| IIA | 8.4 | 70 | 78 | QPDR | No | 5.3 | 71.3 | 1.07 | 2 | 10.8 | 534.8 | Mod |
| IIB | 6.5 | 52 | 67 | QPDR | Yes | 1.12 | 13.7 | 2.88 | 3 | 49.3 | — | Mod |
| IIB | 5.7 | 64 | 72 | QPDR | Yes | 8.5 | 40.8 | 1.46 | 1 | 10.5 | 420.5 | Mod |
| IIB | 9 | 85 | 90 | No/mild | Yes | 23.1 | 52.5 | 1.18 | 2 | 11.5 | 450.6 | Mild |
| IIB | 7.2 | 77 | 93 | No/mild | No | 18.3 | 39 | — | 2 | 10.8 | 455.4 | Mild |
| IIB | 8.8 | 59 | 60 | No/mild | Yes | 12.6 | 53.6 | 1.14 | 2 | 13.8 | 427.4 | Mild |
| IIB | 8.1 | 66 | 79 | No/mild | No | 6 | 43.4 | 1.84 | 2 | 64.6 | — | Mod |
| IIB | 7.8 | 61 | 74 | QPDR | Yes | 0.17 | 9.9 | 3.48 | 3 | 53.8 | — | Mod |
| IIB | 6.9 | 77 | 87 | QPDR | Yes | 346 | 48.7 | 1.37 | 1 | 13.3 | 478.9 | Mod |
| IIB | 6.8 | 58 | 86 | No/mild | Yes | 11 | 54.8 | 1.71 | 2 | 24.7 | — | Mod |
| IIB | 6.2 | 85 | 88 | QPDR | No | 72.6 | 53.7 | 1.31 | 1 | 4.5 | 508.7 | Mod |
| III | 7.2 | 54 | 84 | QPDR | No | — | 15.2 | 6.24 | 2 | 34.8 | — | Severe |
| III | 8 | 74 | 80 | No/mild | Yes | 7.3 | 47.5 | 1.03 | 1 | 8.8 | — | Mod |
| III | 9.8 | 68 | 73 | QPDR | Yes | 3619 | 23.9 | 3.03 | 2 | 38.6 | 696 | Severe |
| III | 7 | 57 | 81 | QPDR | Yes | 394 | 28.5 | 1.87 | 2 | 16.2 | 691 | Severe |
| III | 8.8 | 61 | 64 | No/mild | Yes | 45.5 | 59.7 | 1.05 | 2 | 5.7 | 513.8 | Mod |

TABLE 6

Peptides with significant levels from Kruskai-Wallis two-way comparisons less than 0.05 from resulting from a comparison of DN class 0-1 (protected) and IIb - III (affected) group with ratio of expression.

| Protein Name | Protected MEDIAN | Affected MEDIAN | Fold change (adj) | KW p-value |
|---|---|---|---|---|
| FGB Fibrinogen beta chain precursor | 44.5 | 7 | 3.18 | 0.004 |
| MT-CO2 Cytochrome c oxidase subunit 2* | 110 | 59 | 2.04 | 0.004 |
| NDUFB9 NADH-ubiquinone oxidoreductase B22 subunit* | 13.5 | 9 | 1.59 | 0.005 |
| A2M Alpha-2-macroglobulin precursor | 44 | 12 | 2.69 | 0.005 |
| ALDOA 45 kDa protein* | 20.5 | 6 | 2.52 | 0.005 |
| GDI2 Rab GDP dissociation inhibitor beta | 44 | 16 | 1.85 | 0.008 |
| FGG 50 kDa protein | 45.5 | 17 | 2.43 | 0.008 |
| TPI1 Isoform 1 of Triosephosphate isomerase* | 105 | 44 | 2.05 | 0.008 |
| HP Haptoglobin precursor | 58.5 | 9 | 2.58 | 0.011 |
| SORD Sorbitol dehydrogenase* | 17.5 | 3 | 2.42 | 0.013 |
| AKR1B1 Aldose reductase* | 12.5 | 5 | 1.64 | 0.019 |
| PRDX6 Peroxiredoxin-6 | 29 | 12 | 1.62 | 0.022 |
| VCP Transitional endoplasmic reticulum ATPase | 61 | 37 | 1.66 | 0.022 |
| SOD1 Superoxide dismutase | 41 | 14 | 1.94 | 0.022 |
| MDH1 Malate dehydrogenase, cytoplasmic* | 40.5 | 13 | 2.02 | 0.025 |
| PEBP1 Phosphatidylethanolamine-binding protein 1 | 142 | 26 | 2.14 | 0.028 |
| GAPDH Glyceraldehyde-3-phosphate dehydrogenase* | 374 | 114 | 2.01 | 0.028 |

TABLE 6-continued

Peptides with significant levels from Kruskai-Wallis two-way comparisons less than 0.05 from resulting from a comparison of DN class 0-1 (protected) and IIb - III (affected) group with ratio of expression.

| Protein Name | Protected MEDIAN | Affected MEDIAN | Fold change (adj) | KW p-value |
|---|---|---|---|---|
| GSTT1 Glutathione S-transferase theta 1 | 13 | 0 | 2.47 | 0.033 |
| DPYSL2 Dihydropyrimidinase-related protein 2 | 12 | 3 | 2.74 | 0.033 |
| GOT1 Aspartate aminotransferase, cytoplasmic | 22 | 7 | 1.86 | 0.035 |
| GSTP1 Glutathione S-transferase P | 75.5 | 33 | 1.76 | 0.035 |
| ALDOB Fructose-bisphosphate aldolase B* | 353.5 | 78 | 2.34 | 0.035 |
| FGA Isoform 2 of Fibrinogen alpha chain precursor | 31.5 | 5 | 2.43 | 0.036 |
| GLO1 Lactoylglutathione lyase | 9.5 | 0 | 1.68 | 0.037 |
| BHMT Betaine--homocysteine S-methyltransferase 1 | 85.5 | 16 | 2.96 | 0.039 |
| SELENBP1 54 kDa protein | 26 | 12 | 1.70 | 0.039 |
| PKM2 Isoform M2 of Pyruvate kinase isozymes M1/M2* | 55 | 14 | 2.20 | 0.039 |
| CNDP2 Cytosolic non-specific dipeptidase | 74 | 33 | 2.05 | 0.039 |
| UQCRC2 Cytochrome b-c1 complex subunit 2, mitochondrial precursor | 70 | 37 | 1.72 | 0.043 |
| ENO1 Isoform alpha-enolase of Alpha-enolase* | 134 | 41 | 2.04 | 0.044 |
| LDHB L-lactate dehydrogenase B chain* | 104.5 | 41 | 1.74 | 0.044 |
| BDH2 Isoform 1 of 3-hydroxybutyrate dehydrogenase type 2 | 30 | 6 | 2.29 | 0.047 |
| TALDO1 Transaldolase* | 12.5 | 6 | 1.63 | 0.048 |

*= glucose metabolism proteins

TABLE 7

Plasma metabolites detected with significance in glucose metabolism pathways in protected vs. risk patients. F1P/F6P/G1P/G6P, F16DP/F26DP/G16DP, Lactate, Alpha-glycerophosphate and Glucuronate were significant. Sorbitolis a known metabolite in DN patients. Protected: N = 16; Risk: N = 13; 295 metabolites measured.

| Plasma Metabolites | Fold change | t test |
|---|---|---|
| GLYCOLYSIS | | |
| Glucose | 0.970 | 0.748 |
| F1P/F6P/G1P/G6P | 0.755 | 0.095 |
| Fructose/Glucose/Galactose | 0.986 | 0.813 |
| F16DP/F26DP/G16DP | 0.633 | 0.024 |
| 3-phosphoglycerate | 1.049 | 0.782 |
| Phosphoenolpyruvate | 1.150 | 0.364 |
| Lactate | 0.779 | 0.062 |
| NAD | 1.122 | 0.399 |
| NADP | 1.596 | 0.389 |
| ALDOSE REDUCTASE | | |
| Sorbitol | 0.243 | 0.0003 |
| PKC PATHWAY | | |
| DHAP/Glyceraldehyde 3-phosphate | 1.106 | 0.626 |
| Alpha-glycerophosphate | 0.766 | 0.011 |
| PENTOSE PHOSPHATE PATHWAY | | |
| Ribose-5-phosphate/Ribulose-5-phosphate | 1.014 | 0.941 |
| Erythrose-4-phosphate | 1.638 | 0.638 |
| GLUCURONATE PATHWAY | | |
| UDP-Galactose/UDP-Glucose | 1.228 | 0.150 |
| UDP-Glucuronate | 1.129 | 0.556 |
| Glucuronate | 0.238 | 0.003 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

INCORPORATION BY REFERENCE

The disclosure of each and every publication, including US and foreign patent and pending patent applications, referred to herein is specifically incorporated by reference herein in its entirety.

What is claimed is:

1. A method of diagnosing or predicting risk of developing one or more of DN (diabetic nephropathy) and a microvascular complication in a subject having diabetes, the method comprising:
   providing or obtaining a sample from the subject having diabetes;
   determining the level of a biomarker, wherein said biomarker is PKM2 (pyruvate kinase isozyme M2); and
   comparing the level of the biomarker to the reference level, wherein a lower level of PKM2 protein in the sample as compared to a DN (diabetic nephropathy) reference level, wherein the reference level is the average level of the biomarker in a plurality of individuals who have had diabetes for over 25 years and have not developed a microvascular complication and being the concentration of glomeruli PKM2 protein levels when normalized to actin levels, indicates that the subject having diabetes has, or has an increased risk of developing, DN and/or a microvascular complication relative to a subject having diabetes that has an amount of biomarker equal to or higher than the DN reference level;
   further comprising treating the subject having diabetes and identified as having DN and/or a microvascular complication or having an increased risk of developing DN and/or a microvascular complication by administering to the subject a therapeutically effective amount of an agent that increases the level or activity of PKM2 protein in the subject, and retesting the subject and providing further treatment if the PKM2 protein level is below the reference level, wherein said agent is selected from one or more of PKM2, a nucleotide encoding PKM2,

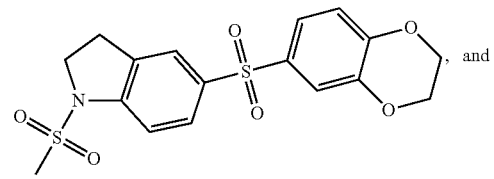, and

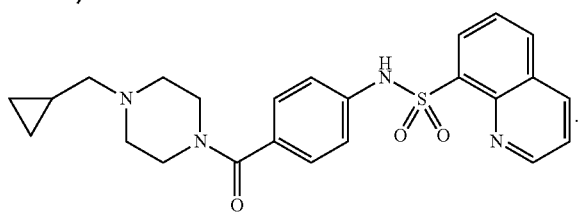.

2. The method of claim 1, wherein a lower level of PKM2 in the sample as compared to a DN reference level indicates that the subject having diabetes has, or has an increased risk of developing, DN relative to a subject having an amount of biomarker that is equal to or higher than the DN reference level.

3. The method of claim 1, wherein the sample comprises plasma, urine or kidney tissue.

4. The method of claim 1, wherein the subject having diabetes has type 1 diabetes.

5. The method of claim 1, wherein the subject having diabetes has type 2 diabetes.

6. A method for determining the prognosis of a microvascular complication in a subject having diabetes and a microvascular complication, comprising:

providing or obtaining a sample from the subject having diabetes;

determining the level of PKM2 protein in the sample from the subject having diabetes; and comparing the level of PKM2 protein to one or more reference levels, wherein a reference level of a biomarker is the average level of the biomarker that is present in a plurality of individuals having diabetes for at least 25 years and who have not developed microvascular complication and being the concentration of glomeruli PKM2protein levels when normalized to actin levels and, wherein a lower level of PKM2protein in the sample as compared to a DN reference level indicates that the subject having diabetes has a poorer prognosis of the microvascular complication relative to a subject having diabetes that has an amount of biomarker that is equal to or higher than the DN reference level;

and administering or causing to be administered to an indicated subject a therapeutically effective amount of an agent that increases the level or activity of PKM2protein in the subject, wherein said agent is selected from one or more of PKM2, a nucleotide encoding PKM2,

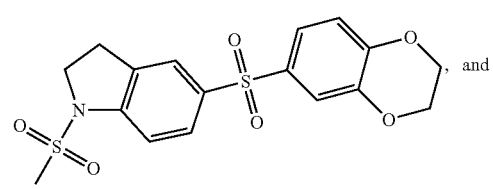, and

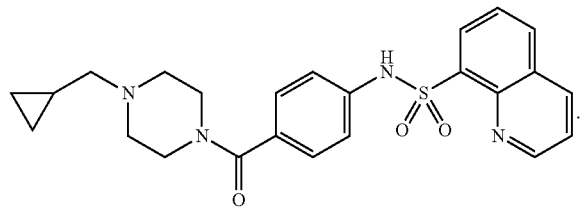

7. The method of claim 6, wherein a lower level of PKM2 in the sample as compared to a DN reference level indicates that the subject having diabetes has a poorer prognosis of DN relative to a subject having an amount of biomarker that is equal to or higher than the DN reference level.

8. A method of determining the effectiveness of a treatment to treat a microvascular complication in a subject having diabetes and being treated for diabetes and/or for the microvascular complication, the method comprising:

providing or obtaining a sample from the treated subject having diabetes;

determining the level of PKM2 protein in the sample from the subject having diabetes; and comparing the level of PKM2 protein to a reference level, wherein the reference level is the level of the biomarker at an earlier time during the treatment or prior to the treatment of the subject having diabetes and being the concentration of glomeruli PKM2 protein levels when normalized to actin levels, wherein a lower level of PKM2 in the sample as compared to a DN reference level indicates that the treatment of the subject is not effective;

and further administering or causing to be administered to an indicated subject a therapeutically effective amount of an agent that increases the level or activity of PKM2 protein in the subject, wherein said agent is selected from one or more of PKM2, a nucleotide encoding PKM2,

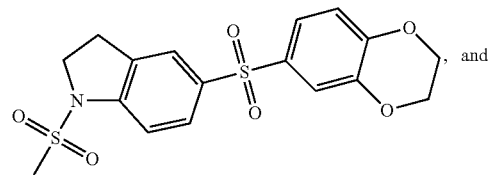, and

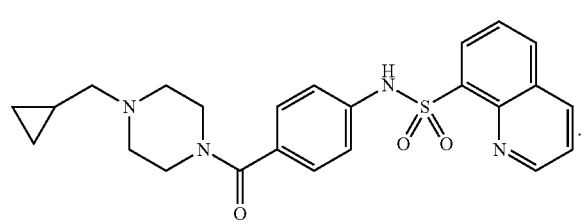

* * * * *

UNITED STATES PATENT AND TRADEMARK OFFICE
CERTIFICATE OF CORRECTION

| | | |
|---|---|---|
| PATENT NO. | : 9,921,221 B2 | Page 1 of 1 |
| APPLICATION NO. | : 14/417023 | |
| DATED | : March 20, 2018 | |
| INVENTOR(S) | : George L. King and Hillary A. Keenan | |

It is certified that error appears in the above-identified patent and that said Letters Patent is hereby corrected as shown below:

Please correct spacing in Claim 6 as follows:

6. A method for determining the prognosis of a microvascular complication in a subject having diabetes and a microvascular complication, comprising:
providing or obtaining a sample from the subject having diabetes;
determining the level of PKM2 protein in the sample from the subject having diabetes; and
comparing the level of PKM2 protein to one or more reference levels, wherein a reference level of a bio-marker is the average level of the biomarker that is present in a plurality of individuals having diabetes for at least 25 years and who have not developed microvascular complication and being the concentration of glomeruli PKM2_protein levels when normalized to actin levels and, wherein a lower level of PKM2_protein in the sample as compared to a DN reference level indicates that the subject having diabetes has a poorer prognosis of the microvascular complication relative to a subject having diabetes that has an amount of bio-marker that is equal to or higher than the DN reference level; and administering or causing to be administered to an indicated subject a therapeutically effective amount of an agent that increases the level or activity of PKM2_protein in the subject, wherein said agent is selected from one or more of PKM2, a nucleotide encoding PKM2,

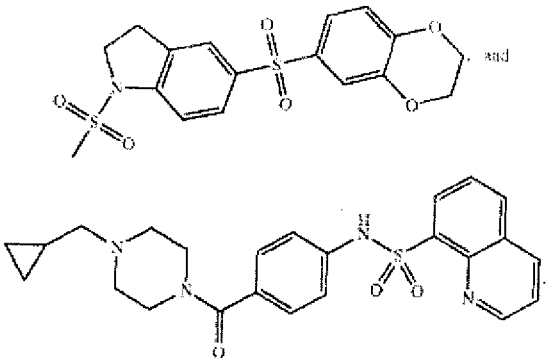

Signed and Sealed this
Twenty-sixth Day of June, 2018

Andrei Iancu
*Director of the United States Patent and Trademark Office*

SEQUENCE LISTING

<160> NUMBER OF SEQ ID NOS: 11

<210> SEQ ID NO 1
<211> LENGTH: 154
<212> TYPE: PRT
<213> ORGANISM: Homo sapiens

<400> SEQUENCE: 1

Met Ala Thr Lys Ala Val Cys Val Leu Lys Gly Asp Gly Pro Val Gln

```
            1               5                  10                 15
Gly Ile Ile Asn Phe Glu Gln Lys Glu Ser Asn Gly Pro Val Lys Val
                20                 25                 30

Trp Gly Ser Ile Lys Gly Leu Thr Glu Gly Leu His Gly Phe His Val
                35                 40                 45

His Glu Phe Gly Asp Asn Thr Ala Gly Cys Thr Ser Ala Gly Pro His
                50                 55                 60

Phe Asn Pro Leu Ser Arg Lys His Gly Pro Lys Asp Glu Glu Arg
65                  70                 75                 80

His Val Gly Asp Leu Gly Asn Val Thr Ala Asp Lys Asp Gly Val Ala
                85                 90                 95

Asp Val Ser Ile Glu Asp Ser Val Ile Ser Leu Ser Gly Asp His Cys
                100                105                110

Ile Ile Gly Arg Thr Leu Val Val His Glu Lys Ala Asp Asp Leu Gly
                115                120                125

Lys Gly Gly Asn Glu Glu Ser Thr Lys Thr Gly Asn Ala Gly Ser Arg
                130                135                140

Leu Ala Cys Gly Val Ile Gly Ile Ala Gln
145                 150

<210> SEQ ID NO 2
<211> LENGTH: 249
<212> TYPE: PRT
<213> ORGANISM: Homo sapiens

<400> SEQUENCE: 2

Met Ala Pro Ser Arg Lys Phe Phe Val Gly Gly Asn Trp Lys Met Asn
1               5                  10                 15

Gly Arg Lys Gln Ser Leu Gly Glu Leu Ile Gly Thr Leu Asn Ala Ala
                20                 25                 30

Lys Val Pro Ala Asp Thr Glu Val Val Cys Ala Pro Pro Thr Ala Tyr
                35                 40                 45

Ile Asp Phe Ala Arg Gln Lys Leu Asp Pro Lys Ile Ala Val Ala Ala
                50                 55                 60

Gln Asn Cys Tyr Lys Val Thr Asn Gly Ala Phe Thr Gly Glu Ile Ser
65                  70                 75                 80

Pro Gly Met Ile Lys Asp Cys Gly Ala Thr Trp Val Val Arg Gly His
                85                 90                 95

Ser Glu Arg Arg His Val Phe Gly Glu Ser Asp Glu Leu Ile Gly Gln
                100                105                110

Lys Val Ala His Ala Leu Ala Glu Gly Leu Gly Val Ile Ala Cys Ile
                115                120                125

Gly Glu Lys Leu Asp Glu Arg Glu Ala Gly Ile Thr Glu Lys Val Val
                130                135                140

Phe Glu Gln Thr Lys Val Ile Ala Asp Asn Val Lys Asp Trp Ser Lys
145                 150                155                160

Val Val Leu Ala Tyr Glu Pro Val Trp Ala Ile Gly Thr Gly Lys Thr
                165                170                175

Ala Thr Pro Gln Gln Ala Gln Glu Val His Glu Lys Leu Arg Gly Trp
                180                185                190

Leu Lys Ser Asn Val Ser Asp Ala Val Ala Gln Ser Thr Arg Ile Ile
                195                200                205

Tyr Gly Gly Ser Val Thr Gly Ala Thr Cys Lys Glu Leu Ala Ser Gln
                210                215                220
```

```
Pro Asp Val Asp Gly Phe Leu Val Gly Gly Ala Ser Leu Lys Pro Glu
225                 230                 235                 240

Phe Val Asp Ile Ile Asn Ala Lys Gln
                245

<210> SEQ ID NO 3
<211> LENGTH: 357
<212> TYPE: PRT
<213> ORGANISM: Homo sapiens

<400> SEQUENCE: 3

Met Ala Ala Ala Lys Pro Asn Asn Leu Ser Leu Val Val His Gly
1               5                   10                  15

Pro Gly Asp Leu Arg Leu Glu Asn Tyr Pro Ile Pro Glu Pro Gly Pro
                20                  25                  30

Asn Glu Val Leu Leu Arg Met His Ser Val Gly Ile Cys Gly Ser Asp
            35                  40                  45

Val His Tyr Trp Glu Tyr Gly Arg Ile Gly Asn Phe Ile Val Lys Lys
        50                  55                  60

Pro Met Val Leu Gly His Glu Ala Ser Gly Thr Val Glu Lys Val Gly
65              70                  75                  80

Ser Ser Val Lys His Leu Lys Pro Gly Asp Arg Val Ala Ile Glu Pro
                85                  90                  95

Gly Ala Pro Arg Glu Asn Asp Glu Phe Cys Lys Met Gly Arg Tyr Asn
            100                 105                 110

Leu Ser Pro Ser Ile Phe Phe Cys Ala Thr Pro Pro Asp Asp Gly Asn
        115                 120                 125

Leu Cys Arg Phe Tyr Lys His Asn Ala Ala Phe Cys Tyr Lys Leu Pro
    130                 135                 140

Asp Asn Val Thr Phe Glu Glu Gly Ala Leu Ile Glu Pro Leu Ser Val
145                 150                 155                 160

Gly Ile His Ala Cys Arg Arg Gly Gly Val Thr Leu Gly His Lys Val
                165                 170                 175

Leu Val Cys Gly Ala Gly Pro Ile Gly Met Val Thr Leu Leu Val Ala
            180                 185                 190

Lys Ala Met Gly Ala Ala Gln Val Val Val Thr Asp Leu Ser Ala Thr
        195                 200                 205

Arg Leu Ser Lys Ala Lys Glu Ile Gly Ala Asp Leu Val Leu Gln Ile
    210                 215                 220

Ser Lys Glu Ser Pro Gln Glu Ile Ala Arg Lys Val Glu Gly Gln Leu
225                 230                 235                 240

Gly Cys Lys Pro Glu Val Thr Ile Glu Cys Thr Gly Ala Glu Ala Ser
                245                 250                 255

Ile Gln Ala Gly Ile Tyr Ala Thr Arg Ser Gly Gly Asn Leu Val Leu
            260                 265                 270

Val Gly Leu Gly Ser Glu Met Thr Thr Val Pro Leu Leu His Ala Ala
        275                 280                 285

Ile Arg Glu Val Asp Ile Lys Gly Val Phe Arg Tyr Cys Asn Thr Trp
    290                 295                 300

Pro Val Ala Ile Ser Met Leu Ala Ser Lys Ser Val Asn Val Lys Pro
305                 310                 315                 320

Leu Val Thr His Arg Phe Pro Leu Glu Lys Ala Leu Glu Ala Phe Glu
                325                 330                 335

Thr Phe Lys Lys Gly Leu Gly Leu Lys Ile Met Leu Lys Cys Asp Pro
            340                 345                 350
```

Ser Asp Gln Asn Pro
         355

<210> SEQ ID NO 4
<211> LENGTH: 418
<212> TYPE: PRT
<213> ORGANISM: Homo sapiens

<400> SEQUENCE: 4

Met Ala Arg Arg Lys Pro Glu Gly Ser Ser Phe Asn Met Thr His Leu
1               5                   10                  15

Ser Met Ala Met Ala Phe Ser Phe Pro Pro Val Ala Ser Gly Gln Leu
            20                  25                  30

His Pro Gln Leu Gly Asn Thr Gln His Gln Thr Glu Leu Gly Lys Glu
        35                  40                  45

Leu Ala Thr Thr Ser Thr Met Pro Tyr Gln Tyr Pro Ala Leu Thr Pro
    50                  55                  60

Glu Gln Lys Lys Glu Leu Ser Asp Ile Ala His Arg Ile Val Ala Pro
65                  70                  75                  80

Gly Lys Gly Ile Leu Ala Ala Asp Glu Ser Thr Gly Ser Ile Ala Lys
                85                  90                  95

Arg Leu Gln Ser Ile Gly Thr Glu Asn Thr Glu Glu Asn Arg Arg Phe
            100                 105                 110

Tyr Arg Gln Leu Leu Leu Thr Ala Asp Asp Arg Val Asn Pro Cys Ile
        115                 120                 125

Gly Gly Val Ile Leu Phe His Glu Thr Leu Tyr Gln Lys Ala Asp Asp
    130                 135                 140

Gly Arg Pro Phe Pro Gln Val Ile Lys Ser Lys Gly Gly Val Val Gly
145                 150                 155                 160

Ile Lys Val Asp Lys Gly Val Val Pro Leu Ala Gly Thr Asn Gly Glu
                165                 170                 175

Thr Thr Thr Gln Gly Leu Asp Gly Leu Ser Glu Arg Cys Ala Gln Tyr
            180                 185                 190

Lys Lys Asp Gly Ala Asp Phe Ala Lys Trp Arg Cys Val Leu Lys Ile
        195                 200                 205

Gly Glu His Thr Pro Ser Ala Leu Ala Ile Met Glu Asn Ala Asn Val
    210                 215                 220

Leu Ala Arg Tyr Ala Ser Ile Cys Gln Gln Asn Gly Ile Val Pro Ile
225                 230                 235                 240

Val Glu Pro Glu Ile Leu Pro Asp Gly Asp His Asp Leu Lys Arg Cys
                245                 250                 255

Gln Tyr Val Thr Glu Lys Val Leu Ala Ala Val Tyr Lys Ala Leu Ser
            260                 265                 270

Asp His His Ile Tyr Leu Glu Gly Thr Leu Leu Lys Pro Asn Met Val
        275                 280                 285

Thr Pro Gly His Ala Cys Thr Gln Lys Phe Ser His Glu Glu Ile Ala
    290                 295                 300

Met Ala Thr Val Thr Ala Leu Arg Arg Thr Val Pro Pro Ala Val Thr
305                 310                 315                 320

Gly Ile Thr Phe Leu Ser Gly Gly Gln Ser Glu Glu Ala Ser Ile
                325                 330                 335

Asn Leu Asn Ala Ile Asn Lys Cys Pro Leu Leu Lys Pro Trp Ala Leu
            340                 345                 350

Thr Phe Ser Tyr Gly Arg Ala Leu Gln Ala Ser Ala Leu Lys Ala Trp

```
                355                 360                 365
Gly Gly Lys Lys Glu Asn Leu Lys Ala Ala Gln Glu Glu Tyr Val Lys
        370                 375                 380
Arg Ala Leu Ala Asn Ser Leu Ala Cys Gln Gly Lys Tyr Thr Pro Ser
385                 390                 395                 400
Gly Gln Ala Gly Ala Ala Ser Glu Ser Leu Phe Val Ser Asn His
                405                 410                 415
Ala Tyr

<210> SEQ ID NO 5
<211> LENGTH: 335
<212> TYPE: PRT
<213> ORGANISM: Homo sapiens

<400> SEQUENCE: 5

Met Gly Lys Val Lys Val Gly Val Asn Gly Phe Gly Arg Ile Gly Arg
1               5                   10                  15
Leu Val Thr Arg Ala Ala Phe Asn Ser Gly Lys Val Asp Ile Val Ala
                20                  25                  30
Ile Asn Asp Pro Phe Ile Asp Leu Asn Tyr Met Val Tyr Met Phe Gln
            35                  40                  45
Tyr Asp Ser Thr His Gly Lys Phe His Gly Thr Val Lys Ala Glu Asn
    50                  55                  60
Gly Lys Leu Val Ile Asn Gly Asn Pro Ile Thr Ile Phe Gln Glu Arg
65                  70                  75                  80
Asp Pro Ser Lys Ile Lys Trp Gly Asp Ala Gly Ala Glu Tyr Val Val
                85                  90                  95
Glu Ser Thr Gly Val Phe Thr Thr Met Glu Lys Ala Gly Ala His Leu
            100                 105                 110
Gln Gly Gly Ala Lys Arg Val Ile Ile Ser Ala Pro Ser Ala Asp Ala
    115                 120                 125
Pro Met Phe Val Met Gly Val Asn His Glu Lys Tyr Asp Asn Ser Leu
130                 135                 140
Lys Ile Ile Ser Asn Ala Ser Cys Thr Thr Asn Cys Leu Ala Pro Leu
145                 150                 155                 160
Ala Lys Val Ile His Asp Asn Phe Gly Ile Val Glu Gly Leu Met Thr
                165                 170                 175
Thr Val His Ala Ile Thr Ala Thr Gln Lys Thr Val Asp Gly Pro Ser
            180                 185                 190
Gly Lys Leu Trp Arg Asp Gly Arg Gly Ala Leu Gln Asn Ile Ile Pro
    195                 200                 205
Ala Ser Thr Gly Ala Ala Lys Ala Val Gly Lys Val Ile Pro Glu Leu
210                 215                 220
Asn Gly Lys Leu Thr Gly Met Ala Phe Arg Val Pro Thr Ala Asn Val
225                 230                 235                 240
Ser Val Val Asp Leu Thr Cys Arg Leu Glu Lys Pro Ala Lys Tyr Asp
                245                 250                 255
Asp Ile Lys Lys Val Val Lys Gln Ala Ser Glu Gly Pro Leu Lys Gly
            260                 265                 270
Ile Leu Gly Tyr Thr Glu His Gln Val Val Ser Ser Asp Phe Asn Ser
    275                 280                 285
Asp Thr His Ser Ser Thr Phe Asp Ala Gly Ala Gly Ile Ala Leu Asn
290                 295                 300
Asp His Phe Val Lys Leu Ile Ser Trp Tyr Asp Asn Glu Phe Gly Tyr
```

```
            305                 310                 315                 320
Ser Asn Arg Val Val Asp Leu Met Ala His Met Ala Ser Lys Glu
                325                 330                 335

<210> SEQ ID NO 6
<211> LENGTH: 531
<212> TYPE: PRT
<213> ORGANISM: Homo sapiens

<400> SEQUENCE: 6

Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
                20                  25                  30

Leu Asp Ile Asp Ser Pro Pro Ile Thr Ala Arg Asn Thr Gly Ile Ile
            35                  40                  45

Cys Thr Ile Gly Pro Ala Ser Arg Ser Val Glu Thr Leu Lys Glu Met
        50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
130                 135                 140

Asp Asn Ala Tyr Met Glu Lys Cys Asp Glu Asn Ile Leu Trp Leu Asp
145                 150                 155                 160

Tyr Lys Asn Ile Cys Lys Val Val Glu Val Gly Ser Lys Ile Tyr Val
                165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
        195                 200                 205

Val Asn Leu Pro Gly Ala Ala Val Asp Leu Pro Ala Val Ser Glu Lys
210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
                245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
        275                 280                 285

Gly Ile Met Val Ala Arg Gly Asp Leu Gly Ile Glu Ile Pro Ala Glu
290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
                325                 330                 335

Lys Pro Arg Pro Thr Arg Ala Glu Gly Ser Asp Val Ala Asn Ala Val
            340                 345                 350
```

```
Leu Asp Gly Ala Asp Cys Ile Met Leu Ser Gly Glu Thr Ala Lys Gly
            355                 360                 365

Asp Tyr Pro Leu Glu Ala Val Arg Met Gln His Leu Ile Ala Arg Glu
        370                 375                 380

Ala Glu Ala Ala Ile Tyr His Leu Gln Leu Phe Glu Glu Leu Arg Arg
385                 390                 395                 400

Leu Ala Pro Ile Thr Ser Asp Pro Thr Glu Ala Thr Ala Val Gly Ala
                405                 410                 415

Val Glu Ala Ser Phe Lys Cys Cys Ser Gly Ala Ile Ile Val Leu Thr
                420                 425                 430

Lys Ser Gly Arg Ser Ala His Gln Val Ala Arg Tyr Arg Pro Arg Ala
            435                 440                 445

Pro Ile Ile Ala Val Thr Arg Asn Pro Gln Thr Ala Arg Gln Ala His
        450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
                485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
            515                 520                 525

Pro Val Pro
        530

<210> SEQ ID NO 7
<211> LENGTH: 434
<212> TYPE: PRT
<213> ORGANISM: Homo sapiens

<400> SEQUENCE: 7

Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                165                 170                 175

Asn Phe Arg Glu Ala Met Arg Ile Gly Ala Glu Val Tyr His Asn Leu
            180                 185                 190
```

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Gly Leu
210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Lys Ser Phe Ile Lys Asp Tyr Pro
        275                 280                 285

Val Val Ser Ile Glu Asp Pro Phe Asp Gln Asp Asp Trp Gly Ala Trp
    290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
                325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ala Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
                405                 410                 415

Leu Gly Ser Lys Ala Lys Phe Ala Gly Arg Asn Phe Arg Asn Pro Leu
            420                 425                 430

Ala Lys

<210> SEQ ID NO 8
<211> LENGTH: 491
<212> TYPE: PRT
<213> ORGANISM: Homo sapiens

<400> SEQUENCE: 8

Met Lys Arg Met Val Ser Trp Ser Phe His Lys Leu Lys Thr Met Lys
1               5                   10                  15

His Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
        35                  40                  45

Leu Asp Lys Lys Arg Glu Glu Ala Pro Ser Leu Arg Pro Ala Pro Pro
    50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
    130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
        195                 200                 205

Ile Gln Lys Leu Glu Ser Asp Val Ser Ala Gln Met Glu Tyr Cys Arg
210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255

Ile Gln Pro Asp Ser Ser Val Lys Pro Tyr Arg Val Tyr Cys Asp Met
            260                 265                 270

Asn Thr Glu Asn Gly Gly Trp Thr Val Ile Gln Asn Arg Gln Asp Gly
        275                 280                 285

Ser Val Asp Phe Gly Arg Lys Trp Asp Pro Tyr Lys Gln Gly Phe Gly
290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335

Pro Thr Glu Leu Leu Ile Glu Met Glu Asp Trp Lys Gly Asp Lys Val
            340                 345                 350

Lys Ala His Tyr Gly Gly Phe Thr Val Gln Asn Glu Ala Asn Lys Tyr
        355                 360                 365

Gln Ile Ser Val Asn Lys Tyr Arg Gly Thr Ala Gly Asn Ala Leu Met
370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
                405                 410                 415

Thr Ser Asp Pro Arg Lys Gln Cys Ser Lys Glu Asp Gly Gly Gly Trp
            420                 425                 430

Trp Tyr Asn Arg Cys His Ala Ala Asn Pro Asn Gly Arg Tyr Tyr Trp
        435                 440                 445

Gly Gly Gln Tyr Thr Trp Asp Met Ala Lys His Gly Thr Asp Asp Gly
    450                 455                 460

Val Val Trp Met Asn Trp Lys Gly Ser Trp Tyr Ser Met Arg Lys Met
465                 470                 475                 480

Ser Met Lys Ile Arg Pro Phe Phe Pro Gln Gln
                485                 490

<210> SEQ ID NO 9
<211> LENGTH: 489
<212> TYPE: PRT
<213> ORGANISM: Homo sapiens

<400> SEQUENCE: 9

Leu Thr Pro Ala Gln Gln Thr Arg Arg Asp Gln Ser Val Pro Val Gly

-continued

```
1               5                   10                  15
Ser Met Ala Thr Lys Cys Gly Asn Cys Gly Pro Gly Tyr Ser Thr Pro
                20                  25                  30
Leu Glu Ala Met Lys Gly Pro Arg Glu Ile Val Tyr Leu Pro Cys
                35                  40                  45
Ile Tyr Arg Asn Thr Gly Thr Glu Ala Pro Asp Tyr Leu Ala Thr Val
            50                  55                  60
Asp Val Asp Pro Lys Ser Pro Gln Tyr Cys Gln Val Ile His Arg Leu
65                  70                  75                  80
Pro Met Pro Asn Leu Lys Asp Glu Leu His His Ser Gly Trp Asn Thr
                85                  90                  95
Cys Ser Ser Cys Phe Gly Asp Ser Thr Lys Ser Arg Thr Lys Leu Val
                100                 105                 110
Leu Pro Ser Leu Ile Ser Ser Arg Ile Tyr Val Val Asp Val Gly Ser
                115                 120                 125
Glu Pro Arg Ala Pro Lys Leu His Lys Val Ile Glu Pro Lys Asp Ile
            130                 135                 140
His Ala Lys Cys Glu Leu Ala Phe Leu His Thr Ser His Cys Leu Ala
145                 150                 155                 160
Ser Gly Glu Val Met Ile Ser Ser Leu Gly Asp Val Lys Gly Asn Gly
                165                 170                 175
Lys Gly Gly Phe Val Leu Leu Asp Gly Glu Thr Phe Glu Val Lys Gly
                180                 185                 190
Thr Trp Glu Arg Pro Gly Gly Ala Ala Pro Leu Gly Tyr Asp Phe Trp
            195                 200                 205
Tyr Gln Pro Arg His Asn Val Met Ile Ser Thr Glu Trp Ala Ala Pro
            210                 215                 220
Asn Val Leu Arg Asp Gly Phe Asn Pro Ala Asp Val Glu Ala Gly Leu
225                 230                 235                 240
Tyr Gly Ser His Leu Tyr Val Trp Asp Trp Gln Arg His Glu Ile Val
                245                 250                 255
Gln Thr Leu Ser Leu Lys Asp Gly Leu Ile Pro Leu Glu Ile Arg Phe
                260                 265                 270
Leu His Asn Pro Asp Ala Ala Gln Gly Phe Val Gly Cys Ala Leu Ser
            275                 280                 285
Ser Thr Ile Gln Arg Phe Tyr Lys Asn Glu Gly Gly Thr Trp Ser Val
            290                 295                 300
Glu Lys Val Ile Gln Val Pro Pro Lys Lys Val Lys Gly Trp Leu Leu
305                 310                 315                 320
Pro Glu Met Pro Gly Leu Ile Thr Asp Ile Leu Leu Ser Leu Asp Asp
                325                 330                 335
Arg Phe Leu Tyr Phe Ser Asn Trp Leu His Gly Asp Leu Arg Gln Tyr
                340                 345                 350
Asp Ile Ser Asp Pro Gln Arg Pro Arg Leu Thr Gly Gln Leu Phe Leu
                355                 360                 365
Gly Gly Ser Ile Val Lys Gly Pro Val Gln Val Leu Glu Asp Glu
            370                 375                 380
Glu Leu Lys Ser Gln Pro Glu Pro Leu Val Val Lys Gly Lys Arg Val
385                 390                 395                 400
Ala Gly Gly Pro Gln Met Ile Gln Leu Ser Leu Asp Gly Lys Arg Leu
                405                 410                 415
Tyr Ile Thr Thr Ser Leu Tyr Ser Ala Trp Asp Lys Gln Phe Tyr Pro
                420                 425                 430
```

```
Asp Leu Ile Arg Glu Gly Ser Val Met Leu Gln Val Asp Val Asp Thr
            435                 440                 445

Val Lys Gly Gly Leu Lys Leu Asn Pro Asn Phe Leu Val Asp Phe Gly
    450                 455                 460

Lys Glu Pro Leu Gly Pro Ala Leu Ala His Glu Leu Arg Tyr Pro Gly
465                 470                 475                 480

Gly Asp Cys Ser Ser Asp Ile Trp Ile
                485

<210> SEQ ID NO 10
<211> LENGTH: 187
<212> TYPE: PRT
<213> ORGANISM: Homo sapiens

<400> SEQUENCE: 10

Met Pro Val Asp Leu Ser Lys Trp Ser Gly Pro Leu Ser Leu Gln Glu
1               5                   10                  15

Val Asp Glu Gln Pro Gln His Pro Leu His Val Thr Tyr Ala Gly Ala
            20                  25                  30

Ala Val Asp Glu Leu Gly Lys Val Leu Thr Pro Thr Gln Val Lys Asn
        35                  40                  45

Arg Pro Thr Ser Ile Ser Trp Asp Gly Leu Asp Ser Gly Lys Leu Tyr
    50                  55                  60

Thr Leu Val Leu Thr Asp Pro Asp Ala Pro Ser Arg Lys Asp Pro Lys
65                  70                  75                  80

Tyr Arg Glu Trp His His Phe Leu Val Val Asn Met Lys Gly Asn Asp
                85                  90                  95

Ile Ser Ser Gly Thr Val Leu Ser Asp Tyr Val Gly Ser Gly Pro Pro
            100                 105                 110

Lys Gly Thr Gly Leu His Arg Tyr Val Trp Leu Val Tyr Glu Gln Asp
        115                 120                 125

Arg Pro Leu Lys Cys Asp Glu Pro Ile Leu Ser Asn Arg Ser Gly Asp
    130                 135                 140

His Arg Gly Lys Phe Lys Val Ala Ser Phe Arg Lys Lys Tyr Glu Leu
145                 150                 155                 160

Arg Ala Pro Val Ala Gly Thr Cys Tyr Gln Ala Glu Trp Asp Asp Tyr
                165                 170                 175

Val Pro Lys Leu Tyr Glu Gln Leu Ser Gly Lys
            180                 185

<210> SEQ ID NO 11
<211> LENGTH: 319
<212> TYPE: PRT
<213> ORGANISM: Homo sapiens

<400> SEQUENCE: 11

Met Ala Ser Ser Ala Ala Gly Cys Val Val Ile Val Gly Ser Gly Val
1               5                   10                  15

Ile Gly Arg Ser Trp Ala Met Leu Phe Ala Ser Gly Gly Phe Gln Val
            20                  25                  30

Lys Leu Tyr Asp Ile Glu Gln Gln Ile Arg Asn Ala Leu Glu Asn
        35                  40                  45

Ile Arg Lys Glu Met Lys Leu Leu Glu Gln Ala Gly Ser Leu Lys Gly
    50                  55                  60

Ser Leu Ser Val Glu Glu Gln Leu Ser Leu Ile Ser Gly Cys Pro Asn
65                  70                  75                  80
```

-continued

```
Ile Gln Glu Ala Val Glu Gly Ala Met His Ile Gln Glu Cys Val Pro
                85                  90                  95
Glu Asp Leu Glu Leu Lys Lys Lys Ile Phe Ala Gln Leu Asp Ser Ile
               100                 105                 110
Ile Asp Asp Arg Val Ile Leu Ser Ser Ser Thr Ser Cys Leu Met Pro
           115                 120                 125
Ser Lys Leu Phe Ala Gly Leu Val His Val Lys Gln Cys Ile Val Ala
       130                 135                 140
His Pro Val Asn Pro Pro Tyr Tyr Ile Pro Leu Val Glu Leu Val Pro
145                 150                 155                 160
His Pro Glu Thr Ala Pro Thr Thr Val Asp Arg Thr His Ala Leu Met
               165                 170                 175
Lys Lys Ile Gly Gln Cys Pro Met Arg Val Gln Lys Glu Val Ala Gly
               180                 185                 190
Phe Val Leu Asn Arg Leu Gln Tyr Ala Ile Ile Ser Glu Ala Trp Arg
           195                 200                 205
Leu Val Glu Glu Gly Ile Val Ser Pro Ser Asp Leu Asp Leu Val Met
       210                 215                 220
Ser Glu Gly Leu Gly Met Arg Tyr Ala Phe Ile Gly Pro Leu Glu Thr
225                 230                 235                 240
Met His Leu Asn Ala Glu Gly Met Leu Ser Tyr Cys Asp Arg Tyr Ser
               245                 250                 255
Glu Gly Ile Lys His Val Leu Gln Thr Phe Gly Pro Ile Pro Glu Phe
               260                 265                 270
Ser Arg Ala Thr Ala Glu Lys Val Asn Gln Asp Met Cys Met Lys Val
           275                 280                 285
Pro Asp Asp Pro Glu His Leu Ala Ala Arg Arg Gln Trp Arg Asp Glu
       290                 295                 300
Cys Leu Met Arg Leu Ala Lys Leu Lys Ser Gln Val Gln Pro Gln
305                 310                 315
```